(12) United States Patent
Molla et al.

(10) Patent No.: US 10,024,777 B2
(45) Date of Patent: Jul. 17, 2018

(54) METHOD AND APPARATUS FOR CHARACTERIZING CLATHRATE HYDRATE FORMATION CONDITIONS EMPLOYING MICROFLUIDIC DEVICE

(71) Applicant: SCHLUMBERGER TECHNOLOGY CORPORATION, Sugar Land, TX (US)

(72) Inventors: Shahnawaz Hossain Molla, Watertown, MA (US); Farshid Mostowfi, Lexington, MA (US); Heng-Joo Ng, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 244 days.

(21) Appl. No.: 15/038,324

(22) PCT Filed: Apr. 23, 2014

(86) PCT No.: PCT/US2014/035141
§ 371 (c)(1),
(2) Date: May 20, 2016

(87) PCT Pub. No.: WO2015/076865
PCT Pub. Date: May 28, 2015

(65) Prior Publication Data
US 2016/0299047 A1     Oct. 13, 2016

Related U.S. Application Data

(60) Provisional application No. 61/907,294, filed on Nov. 21, 2013.

(51) Int. Cl.
*G01N 11/00* (2006.01)
*G01N 11/08* (2006.01)
(Continued)

(52) U.S. Cl.
CPC ........ *G01N 11/08* (2013.01); *B01L 3/502784* (2013.01); *B01L 3/502792* (2013.01);
(Continued)

(58) Field of Classification Search
CPC ......... B01L 3/502784; B01L 3/502797; B01L 7/52; B01L 2300/0883; G01N 11/08;
(Continued)

(56) References Cited

U.S. PATENT DOCUMENTS 6,395,232 B1    5/2002    McBride
8,097,222 B2    1/2012    Scurati
(Continued)

FOREIGN PATENT DOCUMENTS

DE   102011015942 B3    2/2012
EP        2024077 A1    2/2009
(Continued)

OTHER PUBLICATIONS

Ng, H. J., et al., "Equilibrium Phase Composition and Hydrating Conditions in Systems Containing Methanol, Light Hydrocarbons, Carbon Dioxide, and Hydrogen Sulfide", Joint Research Report for GPA and Canadian Gas Processors Association, RR-066 (1983), 44 pages.
(Continued)

*Primary Examiner* — Blake A Tankersley

(57) ABSTRACT

A test method and test apparatus is provided that employs a microfluidic device to characterize properties of a fluid. The microfluidic device has a first inlet port, an outlet port, and a microchannel as part of a fluid path between the first inlet port and the outlet port. While generating a flow of the fluid through the microchannel of the microfluidic device, fluid pressure at the first inlet port of the microfluidic device is measured and recorded in conjunction with varying the controlled temperature of the microchannel of the microflu-
(Continued)

idic device to characterize the properties of the fluid that flows through the microchannel of the microfluidic device. The properties of the fluid can relate to the clathrate hydrate formation condition of the fluid at the pressure of the flow through the microchannel of the microfluidic device.

35 Claims, 10 Drawing Sheets

(51) Int. Cl.

| | | |
|---|---|---|
| *B01L 3/00* | (2006.01) | |
| *G01N 21/05* | (2006.01) | |
| *G01N 33/24* | (2006.01) | |
| *G01N 33/28* | (2006.01) | |
| *G01N 35/10* | (2006.01) | |
| *G01N 21/88* | (2006.01) | |
| *B01L 7/00* | (2006.01) | |
| *C10L 3/10* | (2006.01) | |
| *G01N 21/03* | (2006.01) | |

(52) U.S. Cl.
CPC ......... *G01N 21/05* (2013.01); *G01N 21/8851* (2013.01); *G01N 33/24* (2013.01); *G01N 33/28* (2013.01); *G01N 35/1095* (2013.01); *B01J 2219/00049* (2013.01); *B01L 7/52* (2013.01); *B01L 2200/146* (2013.01); *B01L 2200/147* (2013.01); *B01L 2300/0627* (2013.01); *B01L 2300/0816* (2013.01); *B01L 2300/0883* (2013.01); *B01L 2300/14* (2013.01); *B01L 2300/1894* (2013.01); *C10L 3/107* (2013.01); *G01N 21/0332* (2013.01); *G01N 2021/0346* (2013.01); *G01N 2035/1034* (2013.01)

(58) Field of Classification Search
CPC ............... G01N 21/8851; G01N 21/05; G01N 21/0332; G01N 2021/052; G01N 2021/056; G01N 2035/1034; G01N 2011/002

See application file for complete search history.

(56) References Cited

U.S. PATENT DOCUMENTS

| | | | |
|---|---|---|---|
| 2004/0099060 A1* | 5/2004 | Kijlstra | G01N 11/08 73/714 |
| 2006/0193730 A1 | 8/2006 | Rosenstein et al. | |
| 2008/0131323 A1 | 6/2008 | Kuczenski et al. | |
| 2011/0243790 A1 | 10/2011 | Cheung et al. | |
| 2011/0307186 A1* | 12/2011 | Mostowfi | B01L 3/5027 702/24 |
| 2012/0052563 A1 | 3/2012 | Liang et al. | |

FOREIGN PATENT DOCUMENTS

| | | |
|---|---|---|
| WO | WO2005022105 A1 | 3/2005 |
| WO | WO2013070283 A1 | 5/2013 |

OTHER PUBLICATIONS

Clarke, M. et al, "Determination of the intrinsic rate of ethane gas hydrate decomposition", Chemical Engineering Science, 2000, 55(21), pp. 4869-4883.

Clarke, M. A. et al., "Measuring and modelling the rate of decomposition of gas hydrates formed from mixtures of methane and ethane", Chemical Engineering Science, 2001, 56(16), pp. 4715-4724.

Hammerschmidt, E.G., "Formation of Gas Hydrates in Natural Gas Transmission Lines", Industrial & Engineering Chemistry, 1934, 26(8), pp. 851-855.

Koh, C. A. et al., "Fundamentals and Applications of Gas Hydrates", Annual Review of Chemical and Biomolecular Engineering, 2011, 2, pp. 237-257.

Sloan, E. D. et al., "Experimental Methods and Measurements of Hydrate Properties", in Clathrate Hydrates of Natural Gases, Third Edition, Taylor & Francis, 2007, pp. 320-326.

Sloan, E. D. et al., "Experimental Methods and Measurements of Hydrate Properties", in Clathrate Hydrates of Natural Gases, Third Edition, Taylor & Francis, 2007, pp. 379-387.

Tohidi, B. et al., "Visual observation of gas-hydrate formation and dissociation in synthetic porous media by means of glass micromodels", Geology, 2001, 29(9), pp. 867-870.

White, F. M., "Solutions of the Newtonian Viscous-Flow Equations" in Viscous Fluid Flow, McGraw Hill, New York, NY, 2005, pp. 107-117.

Search Report of EP Patent Application No. 14863859.6 dated Jun. 26, 2017, 3 pages.

Exam Report of EP Patent Application No. 14863859.6 dated Jul. 13, 2017, 5 pages.

* cited by examiner (T=12°C)

(T=5°C)

METHOD AND APPARATUS FOR CHARACTERIZING CLATHRATE HYDRATE FORMATION CONDITIONS EMPLOYING MICROFLUIDIC DEVICE

CROSS-REFERENCE TO RELATED APPLICATIONS

The present application claims priority from U.S. Provisional Application 61/907,294, filed on Nov. 21, 2013, herein incorporated by reference in its entirety.

BACKGROUND

Field

The present application relates to the detection of the formation of clathrate hydrates and in particular, but not exclusively, to the measurement of pressures and corresponding temperatures at which clathrate hydrates are found to form.

Related Art

A clathrate is a chemical substance consisting of a lattice that traps or contains molecules. Clathrate hydrates (also referred to as gas clathrates, gas hydrates, clathrates, or hydrates) are crystalline water-based solids physically resembling ice, in which small non-polar molecules (typically gases) or polar molecules with large hydrophobic moieties are encapsulated or trapped inside "cages" of hydrogen bonded water molecules. In other words, clathrate hydrates are clathrate compounds in which the host molecule is water and the guest molecule is typically a gas or liquid. Most low molecular weight gases (such as oxygen, hydrogen, nitrogen, carbon dioxide, methane, hydrogen sulfide, argon, krypton, and xenon) as well as some higher hydrocarbons will form hydrates at suitable temperatures and pressures. Clathrate hydrates are not chemical compounds, as the sequestered molecules are never bonded to the lattice. The formation and decomposition of clathrate hydrates are first order phase transitions, not chemical reactions.

Clathrate hydrates are of interest in the petroleum industry, particularly with respect to producing, transporting and processing of natural gas and petroleum fluids. In these applications, the clathrate hydrates are typically composed of water and one or more of the following eight guest molecules: methane, ethane, propane, isobutane, normal butane, nitrogen, carbon dioxide, and hydrogen sulfide. Other guest molecules can include ethane, nitrous oxide, acetylene, vinyl chloride, methyl bromide, ethyl bromide, cyclopropane, methyl mercaptan, sulfur dioxide, argon, krypton, oxygen, xenon, trimethylene oxides, and others.

Clathrate hydrates can be a problem for development and production in the petroleum industry when working at high pressures and cold temperatures, possibly resulting in production delays and "blowouts" of wells. Gas hydrate formation during deepwater offshore drilling is a well-recognized operational hazard. At present, most common hydrate removal techniques include depressurization of the flow line, mechanical removal, and heating. Heat is supplied to raise the temperature in the section of the pipe where hydrate formation is expected. However, it is imperative to ensure uniform heating throughout the region of hydrate formation. In several cases, poorly controlled heating has caused release of gas (due to melting of hydrate), resulting in fatal accidents due to rapid increase in localized pressure in the pipe. Chemical additives have also been used to control the hydrate kinetics in order to prevent formation of hydrate nuclei and slow down their growth. These chemical inhibitors can cost millions of dollars for offshore wells.

The equilibrium clathrate hydrate formation point is the temperature (at a given pressure) or the pressure (at a given temperature) where the initial small quantity of clathrate hydrate appears after a sufficiently long time. This point corresponds to the thermodynamic formation point of clathrate hydrates. Laboratory measurements are conducted by forming some clathrate hydrate and then slowly heating or de-pressurizing the sample until it all dissociates. The point on the dissociation curve where no clathrate hydrate remains is identical to the thermodynamic formation point. In practice, there is a delay in forming clathrate hydrate until a lower temperature or higher pressure is reached. Before the thermodynamic formation point is reached hydrate cannot form. This is known as the stability limit. Beyond the stability limit clathrate hydrate can form but may not do so for a long time.

Most commercial clathrate hydrate phase equilibrium measurements are conducted in macroscopic systems which allow visual confirmation of clathrate hydrate formation and dissociation as the pressure or temperature is varied. A comprehensive review of the systems used for hydrate phase equilibrium measurements can be found in Sloan, E. D. and C. Koh, "Clathrate Hydrates of Natural Gases," Third Edition, Taylor & Francis, 2007, pp. 320-326. These systems typically consist of a stainless steel container (hydrate cell) with a sight-glass, capable of withstanding high pressure. The cell is designed with different mechanisms to impart vigorous agitation on the fluids to enhance mixing between the gas and the liquid phase. The agitation is necessary for surface renewal and exposure of the liquid to the hydrate former. The agitation reduces the metastability during the clathrate hydrate formation stage. The source of agitation varies widely among the systems; namely, physical rocking of the hydrate cell, rotation, electromagnetic agitation, magnetic stirring.

Visual techniques can also be used to determine the temperature and pressure conditions of clathrate hydrate formation in reservoir fluids containing natural gas, carbon dioxide, hydrogen sulfide, gas condensate, or conventional oil in the presence of water. The visual techniques involve charging known amounts of hydrocarbon and aqueous fluids into the cells and then cycling the temperature over a range of values while maintaining a constant pressure. Visual detection of the formation and dissociation (melting) of clathrate hydrate crystals during heating and cooling is used to determine the clathrate hydrate formation conditions.

Clathrate hydrate equilibrium measurements can also be conducted in blind cells (autoclaves) based only on pressure-temperature trace. Mechanical mixing is provided by a magnetically coupled impeller inside the cell and controlled by an external motor. Several mesoscopic methods are also available for clathrate hydrate phase measurement such as methods that employ a light scattering/reflectance method and synthetic porous media. In addition to measuring clathrate hydrate equilibrium, the light scattering method also measures the changes in the hydrate particle size during clathrate hydrate formation and dissociation. The synthetic porous media method can use a glass micro-model to demonstrate that clathrate hydrate formation in porous media can occur at the gas-liquid interface and also from dissolved gas in the liquid.

The clathrate hydrate equilibrium measurement methods produce accurate measurements supported by thermodynamic models. However, the equipment and setup for these methods are designed for use in laboratory environments.

Due to the large volume of the test samples (several hundred cc), the metastable period prior to detectable clathrate hydrate formation is usually long (hours to days). Additionally, the handling of large sample volumes at high pressure poses potential hazards.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a test method and a test apparatus that employs a microfluidic device to characterize properties of a fluid. The microfluidic device has a first inlet port, an outlet port, and a microchannel as part of a fluid path between the first inlet port and the outlet port. While generating a flow of the fluid through the microchannel of the microfluidic device, the fluid pressure at the first inlet port of the microfluidic device is measured and recorded in conjunction with varying the controlled temperature of the microchannel of the microfluidic device to characterize the properties of the fluid that flows through the microchannel of the microfluidic device. The properties of the fluid can relate to the clathrate hydrate formation condition of the fluid at the pressure of the flow through the microchannel of the microfluidic device.

In one aspect, the test apparatus includes a temperature-controlled surface that is thermally-coupled to the microfluidic device and configured to control the temperature of the microchannel of the microfluidic device. A first pump is fluidly coupled to the first inlet port of the microfluidic device. The first pump is operated to generate a flow of the fluid through the microchannel of the microfluidic device. A first pressure sensor is configured to measure fluid pressure at the first inlet port of the microfluidic device. The test apparatus further includes means for recording fluid pressure measured by the first pressure sensor over time as the temperature-controlled surface is operated to vary the temperature of the microchannel of the microfluidic device to characterize properties of the fluid. The test apparatus can further include at least one temperature sensor for measuring temperature characteristic of the microchannel of the microfluidic device. The properties of the fluid can relate to the clathrate hydrate formation condition of the fluid at the pressure of the flow through the microchannel of the microfluidic device. For example, the properties of the fluid can include the clathrate hydrate formation temperature of the fluid at the pressure of the flow through the microchannel of the microfluidic device.

In one embodiment, the test apparatus further includes a light source and camera configured to capture images of the microchannel of the microfluidic device. The test apparatus can include means for evaluating or analyzing the images captured by the camera to determine whether such images include information that indicates the presence of clathrate hydrate formation in the fluid that flows through the microchannel of the microfluidic device.

The test apparatus can also include means for evaluating or analyzing the fluid pressure measured by the first pressure sensor over time as the temperature-controlled surface is operated to vary temperature of the microchannel of the microfluidic device to determine whether the fluid pressure measured by the first pressure sensor over time includes characteristics that indicate the presence of clathrate hydrate formation in the fluid that flows through the microchannel of the microfluidic device. The characteristics that indicate the presence of clathrate hydrate formation in the fluid that flows through the microchannel of the microfluidic device can be selected from the group consisting of i) an increase in the fluid pressure measured by the first pressure sensor and ii) oscillations in the fluid pressure measured by the first pressure sensor.

The first pump can be configured to supply a reservoir fluid to the first inlet port of the microfluidic device such that the fluid flowing through the microchannel of the microfluidic device includes the reservoir fluid to characterize properties that relate to the clathrate hydrate formation condition of the reservoir fluid at the pressure of the flow through the microchannel of the microfluidic device.

The microfluidic device can further include a second inlet port as well as a mixing section that is fluidly coupled to both the first inlet port and the second inlet port. The microchannel can be part of a fluid path between the mixing section and the outlet port of the microfluidic device. A second pump can be fluidly coupled to the second inlet port of the microfluidic device. The first and second pumps can be configured to generate the flow of the fluid through the microchannel of the microfluidic device. A second pressure sensor can be configured to measure fluid pressure at the second inlet port of the microfluidic device. The test apparatus can further include means for recording fluid pressures measured by the second pressure sensor over time as the temperature-controlled surface is operated to vary temperature of the microchannel of the microfluidic device to characterize properties of the fluid.

The test apparatus can further include means for evaluating or analyzing the fluid pressures measured by the first and second pressure sensors over time as the temperature-controlled surface is operated to vary temperature of the microchannel of the microfluidic device to determine whether the fluid pressures measured by the first and second pressure sensor over time include characteristics that indicate the presence of clathrate hydrates in the fluid that flows through the microchannel of the microfluidic device.

In another aspect, the test method can include operations that capture images of the microchannel of the microfluidic device while generating the flow of the fluid through the microchannel of the microfluidic device. The captured images can be evaluated or analyzed to determine whether such images include information that indicates the presence (or absence) of clathrate hydrate formation in the fluid that flows through the microchannel of the microfluidic device.

The test method can also include operations that evaluate or analyze the fluid pressure at the first inlet port over time as the temperature of the microchannel of the microfluidic device is varied to determine whether the fluid pressure measured by the first pressure sensor over time includes characteristics that indicate the presence of clathrate hydrate formation in the fluid that flows through the microchannel of the microfluidic device. The characteristics that indicate the presence of clathrate hydrate formation in the fluid that flows through the microchannel of the microfluidic device can be selected from the group consisting of i) an increase in the fluid pressure at the first inlet port and ii) oscillations in the fluid pressure at the first inlet port.

The microfluidic device can further include a second inlet port as well as a mixing section that is fluidly coupled to both the first inlet port and the second inlet port. The microchannel can be part of a fluid path between the mixing section and the outlet port of the microfluidic device. In this case, the test method can include measuring and recording fluid pressure at the second inlet port of the microfluidic device in conjunction with varying temperature of the microchannel of the microfluidic device while generating the flow of the fluid through the microchannel of the microfluidic device to characterize properties of the fluid that flows through the microchannel of the microfluidic device.

The test method can also include operations that evaluate or analyze the fluid pressures at the first and second inlet ports over time as the temperature of the microchannel of the microfluidic device is varied to determine whether the fluid pressures at the first and second inlet ports over time includes characteristics that indicate the presence (or absence) of clathrate hydrate formation in the fluid that flows through the microchannel of the microfluidic device.

In another aspect, a test method is provided that employs a microfluidic device to characterize properties that relate to the clathrate hydrate formation condition of a fluid that includes a reservoir fluid component. The microfluidic device has a first inlet port, an outlet port, and a microchannel as part of a fluid path between the first inlet port and the outlet port. While generating a flow of the fluid through the microchannel of the microfluidic device, fluid pressure at the first inlet port of the microfluidic device is measured and recorded in conjunction with varying temperature of the microchannel of the microfluidic device to characterize properties that relate to the clathrate hydrate formation condition of the fluid at the pressure of the flow through the microchannel of the microfluidic device.

The test method can include operations that configure a first pump to supply a reservoir fluid to the first inlet port of the microfluidic device such that the fluid flowing through the microchannel of the microfluidic device includes the reservoir fluid.

The test method can also include operations that control the temperature of the microchannel of the microfluidic device to a temperature where clathrate hydrates dissociate at the pressure of the flow through the microchannel of the microfluidic device, and measure and record a steady state fluid pressure at the first inlet port of the microfluidic device.

The test method can also include operations that iteratively decrease the temperature of the microchannel of the microfluidic device by a predetermined step value while evaluating or analyzing the fluid pressure at the first inlet port over time to determine whether the fluid pressures at the first inlet port over time include characteristics that indicate the presence of clathrate hydrate formation in the fluid that flows through the microchannel of the microfluidic device.

The test method can also include operations that, subsequent to determining the presence of clathrate hydrate formation in the fluid that flows through the microchannel of the microfluidic device, increase the temperature of the microchannel of the microfluidic device to a temperature where clathrate hydrates dissociate at the pressure of the flow through the microchannel of the microfluidic device. With the temperature of the microchannel of the microfluidic device controlled at the temperature where clathrate hydrates dissociate at the pressure of the flow through the microchannel of the microfluidic device, the fluid pressure at the first inlet port over time is evaluated or analyzed to determine whether the fluid pressures at the first inlet port over time include characteristics that indicate the absence of clathrate hydrate formation in the fluid that flows through the microchannel of the microfluidic device.

The microfluidic device can further include a second inlet port as well as a mixing section that is fluidly coupled to both the first inlet port and the second inlet port. The microchannel can be part of a fluid path between the mixing section and the outlet port of the microfluidic device. In this case, the test method can include operations that configure a first pump to supply a reservoir fluid to the first inlet port of the microfluidic device and configure a second pump to supply an additive to the second inlet port of the microfluidic device such that the fluid that flows through the microchannel of the microfluidic device includes a mixture of the reservoir fluid and the additive. These operations are useful in studying the effects of different hydrate inhibitor additives on the particular reservoir fluid for different flow pressures and/or additive concentrations as desired. Such operations can be used to optimize a strategy for reservoir fluid production and/or transportation that minimizes the formation of clathrate hydrates during these processes.

DETAILED DESCRIPTION

Figure 1:
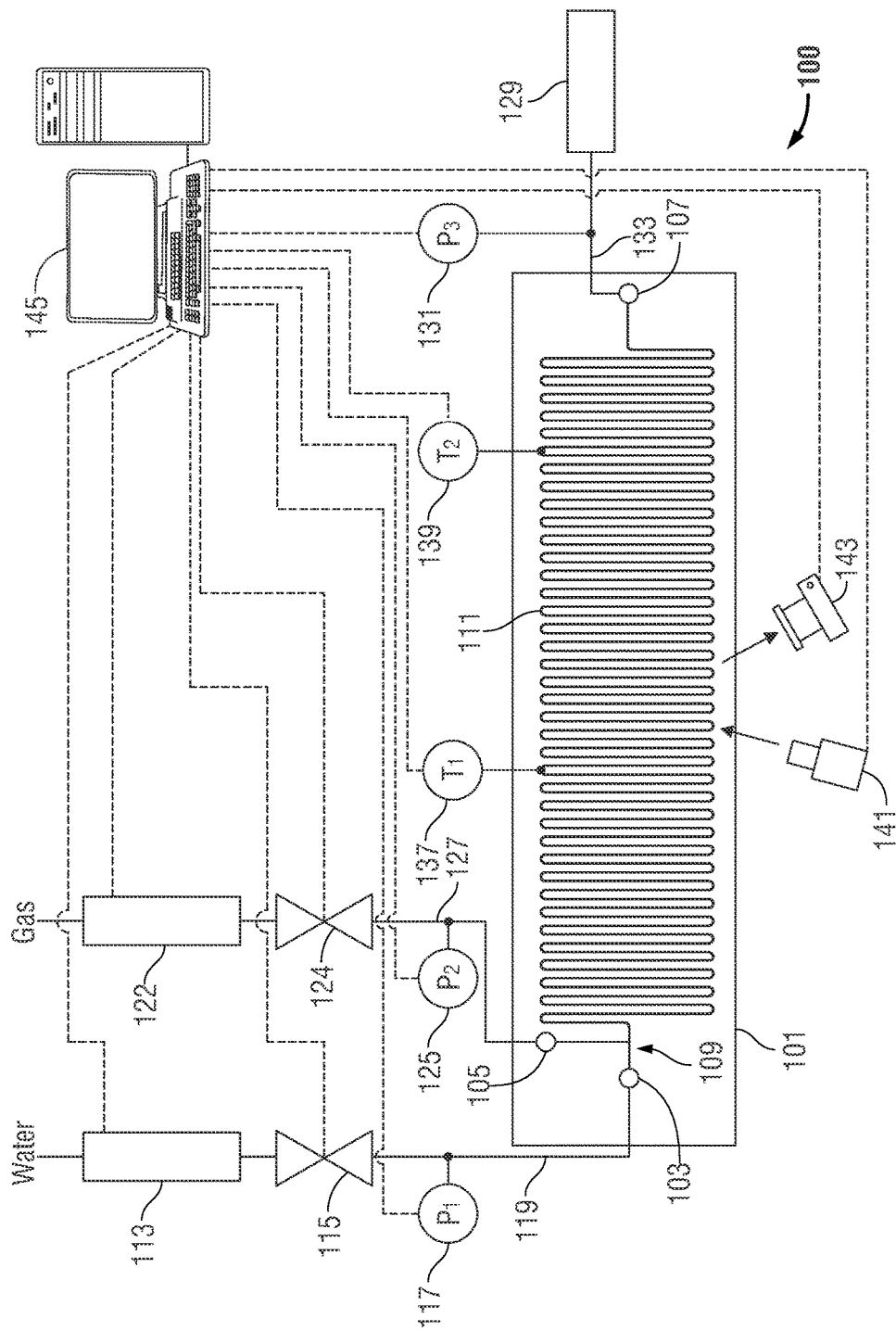
FIG. 1 is a schematic diagram of a test apparatus according to an embodiment of the present disclosure.

Illustrative embodiments of the present disclosure are described below. In the interest of clarity, not all features of an actual implementation are described in this specification. It will be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. Further, like reference numbers and designations in the various drawings indicated like elements.

For the purposes of this disclosure, the term "reservoir fluid" means a fluid stored in or transmitted from a subsurface body of permeable rock. Thus "reservoir fluid" may include, without limitation, hydrocarbon fluids, saline fluids such as saline water, as well as other formation water, and other fluids such as carbon dioxide in a supercritical phase.

Moreover, for the purposes of this disclosure, the term "microfluidic device" means a device having a fluid-carrying channel exhibiting a width within a range of tens to hundreds of micrometers, but exhibiting a length that is many times longer than the width of the channel. Similarly the term "microchannel" means a fluid-carrying channel exhibiting a width within a range of tens to hundreds of micrometers. Although many of the microchannels described herein are of rectangular cross section due to the practicalities of fabrication techniques, the cross section of a microchannel can be of any shape, including round, oval, ellipsoid, and square.

In order to determine the equilibrium clathrate hydrate formation temperature of a fluid sample, it is necessary to lower the temperature of the fluid sample below its equilibrium clathrate hydrate formation temperature. The time required for the temperature equilibration depends on the volume of the fluid sample. In addition, since clathrate hydrate formation is influenced by the cooling rate, the fluid sample must be cooled down at a specified rate. These considerations are equally valid when the fluid sample is heated to measure the temperature of clathrate hydrate dissociation.

A microfluidic device employs one or more microchannels (capillaries) where the surface area in contact with fluid flowing in the microchannel is relatively large compared to the volume of the fluid flowing through the microchannel. As a result, the heat transfer between the sample and its surroundings is rapid and the temperature of the fluid in the microchannel can be changed rapidly. Also, due to the small dimensions of the microchannel, the sample volume required in the microfluidic device amounts to only a few micro-liters of liquid.

Therefore, the testing methods and apparatus described herein utilize a microfluidic device for rapid and accurate detection of clathrate hydrates formed in a fluid sample flowing through the microfluidic device, the temperature of which can be precisely controlled. The pressure-driven flow of the fluid sample in the microfluidic device is monitored using pressure sensors to identify properties of the clathrate hydrate formation condition (or the clathrate hydrate dissociation condition).

Figure 2:
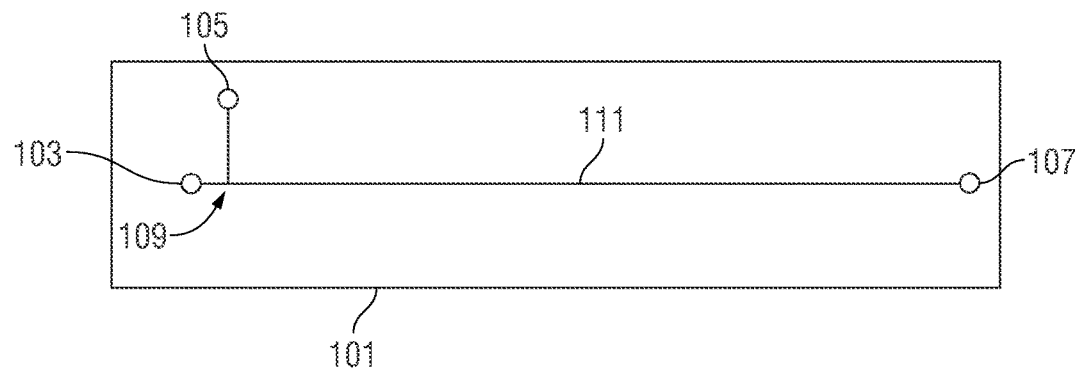
FIG. 2 is a schematic top view of another embodiment of a microfluidic device that can be used as part of the test apparatus of FIG. 1.

As shown in FIG. 1, an exemplary test apparatus 100 includes a microfluidic device 101 that includes a first inlet port 103, a second inlet port 105 and an outlet port 107. The microfluidic device 101 also includes an internal mixing section 109 (which can be a t-junction as shown) that is fluidly coupled to both the first inlet port 103 and the second inlet port 105 as well as to a microchannel 111 that extends between the mixing section 109 and the outlet port 107. In the embodiment shown in FIG. 1, the microchannel 111 can form a serpentine pattern, thus allowing the microchannel 111 to extend a significant length but occupy a relatively small area. For example, the length of the serpentine pattern can be 1.7 meters over an area of 80 mm×15 mm. In another embodiment shown in FIG. 2, the microchannel 111 can extend in a linear manner between the mixing section 109 and the outlet port 107.

Figure 3:
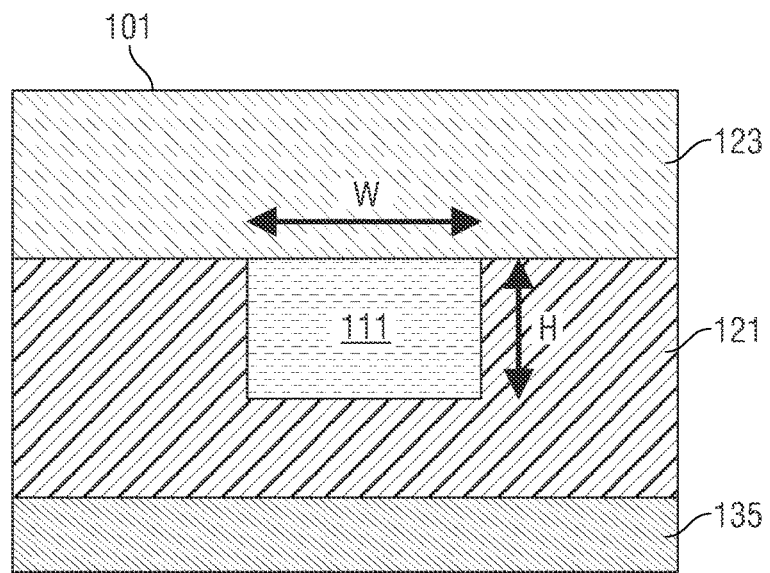
FIG. 3 is a schematic cross-sectional view of an exemplary embodiment of the microfluidic device of FIG. 1 or FIG. 2 in conjunction with a temperature-controlled heating-cooling surface that is placed in thermal contact with the microfluidic device.

In one embodiment shown in FIG. 3, the mixing section 109 and the microchannel 111 of the microfluidic device 101 can be defined by etching the planar surface of a first substrate 121. The first substrate 121 can be made of silicon (e.g., a conventional silicon-on-insulator wafer) or other suitable material. A second substrate 123 can be sealably bonded to the planar surface of the first substrate 121 that has been etched to form the mixing section 109 and the microchannel 111. The bonding can employ an anodic bonding method after careful cleaning of the bonding surfaces of the first and second substrates 121, 123. The second substrate 123 can define the first and second inlet ports 103, 105 and the outlet port 107 that are in fluid communication with the mixing section 109 and the microchannel 111. The second substrate 123 can be made of glass, such as borosilicate glass (e.g., a borosilicate glass manufactured by Schott North America, Inc. of Elmsford, N.Y., USA, or by Corning Incorporated of Corning, N.Y., USA) or other suitable material. The flow paths of the mixing section 109 and the microchannel 111 can have uniform rectangular cross-sections formed in the first substrate as shown in FIG. 3. In one example, such rectangular cross-sections have a width (W) of 100 μm and a height (H) of 50 μm. However, the cross-sections can have other geometric shapes as desired.

The test apparatus 100 also includes an electrically-controlled reservoir and pump 113 that is loaded with a quantity of water (preferably deionized water). The reservoir and pump 113 has an outlet that is fluidly coupled to an electrically-controlled valve 115. The reservoir and pump 113 and the valve 115 are operated to inject the water (preferably at or near a constant pressure) into the first inlet port 103 of the microfluidic device 101. A pressure sensor 117 (such as the Sensotreme sensor available from Sensotreme GmbH of Ramsen, Switzerland) can be disposed within the supply line 119 between the valve 115 and the first inlet port 103 to monitor the pressure of the water in the supply line 119. The reservoir and pump 113 can be an electrically-controlled syringe pump, such as the ISCO 65D available from Teledyne Technologies Inc. of Lincoln, Nebr., USA. The supply line 119 can include an in-line filter that removes particulate matter that could potentially clog the microchannel 111 of the microfluidic device 101. The reservoir and pump 113, the valve 115, and the supply line 119 can all operate at or near ambient temperature.

The test apparatus 100 also includes an electrically-controlled reservoir and pump 122 that is loaded with a quantity of gas. The reservoir and pump 122 has an outlet that is fluidly coupled to an electrically-controlled valve 124. The reservoir and pump 122 and the valve 124 are operated to inject the gas (preferably at or near a constant pressure) into the second inlet port 105 of the microfluidic device 101. A pressure sensor 125 (such as the Sensotreme sensor available from Sensotreme GmbH of Ramsen, Switzerland) can be disposed within the supply line 127 between the valve 124 and the second inlet port 105 to monitor the pressure of the gas in the supply line 127. The reservoir and pump 122 can be an electrically-controlled syringe pump, such as the ISCO 65D available from Teledyne Technologies Inc. of Lincoln, Nebr., USA. The supply line 127 can include an in-line filter that removes particulate matter that could potentially clog the microchannel 111 of the microfluidic device 101. The reservoir and pump 122, the valve 124, and the supply line 127 can all operate at or near ambient temperature.

The outlet port 107 of the microfluidic device 101 is fluidly coupled to a collection chamber 129. The pressure of the collection chamber 129 can be controlled to maintain constant pressure. A pressure sensor 131 (such as the Sensotreme sensor available from Sensotreme GmbH of Ramsen, Switzerland) can be disposed within an outlet line 133 between the outlet port 107 and the collection chamber 129 to monitor the pressure of the fluid flowing in the outlet line 133.

As best shown in FIG. 3, the microfluidic device 101 can be supported by (or otherwise thermally coupled to) a temperature-controlled cooling/heating surface 135 that provides for temperature control of the microfluidic device 101 (including the microchannel 111 therein) independent of the temperature of the rest of the apparatus. The temperature-controlled cooling/heating surface 135 may also be embedded in substrate 121 using microfabrication technology.

Turning back to FIG. 1, one or more temperature sensors (for example two shown as temperature sensors 137 and 139) can be used to monitor the temperature of the microchannel 111 of the microfluidic device 101. The temperature sensors can be thermocouples, such as the Omega 5TC-TT-K 40-36 available from Omega Engineering Inc. of Laval, Quebec, Canada. The temperature-controlled cooling/heating surface 135 can be used to control the temperature of specific sections of the microchannel 111 instead of the entire microfluidic device 101. In this case, the temperature sensors can be used to measure the temperature gradient along the sections of the microchannel 111 for control of the temperature gradient by cooling/heating surface 135. The temperature-controlled cooling/heating surface 135 can be a thermo-electric plate, such as a TEC model TC-36-25 RS485, available from TE Technology, Inc. of Traverse City, Mich., USA.

A light source 141 and a camera 143 can be arranged to capture high resolution images of the microchannel 111 of the microfluidic device 101 to detect the presence (or absence) of clathrate hydrates in the microchannel 111 as described below.

The test apparatus 100 also includes a controller and/or computer processing system 145 that includes control logic that interfaces to the electrically-controlled reservoir and pumps 113 and 122 via wired or wireless signal paths therebetween for control of the operation of the pumps 113 and 122, that interfaces to the electrically-controlled valves 115 and 124 via wired or wireless signal paths therebetween for control of the operation of the valves 115 and 124, that interfaces to the temperature-controlled cooling/heating surface 135 via wired or wireless signal paths therebetween to provide for temperature control of the microfluidic device 101 (or the microchannel 111 or portions thereof), that interfaces to the pressure sensors 117 and 125 and 131 via wired or wireless signal paths therebetween for pressure measurements and recordation of such pressure measurements during operation of the test apparatus 100, and that interfaces to the temperature sensors 137 and 139 via wired or wireless signal paths therebetween for temperature measurements and recordation of such temperature measurements during operation of the test apparatus 100. The controller and/or computer processing system 145 can also interface to the light source 141 and/or to the camera 143 via wired or wireless signal paths therebetween to capture high resolution images of the microchannel 111 and recordation of such high resolution images and possibly display of such high resolution images during operation of the test apparatus 100. The control logic of the controller and/or computer processing system 145 (which can be embodied in software that is loaded from persistent memory and executed in the computing platform of the computer processing system 145) is configured to control the different parts of the test apparatus 100 to carry out a sequence of operations (workflow) that characterizes properties related to clathrate hydrate formation condition (such as the clathrate hydrate formation temperature) of the fluid that flows through the microchannel 111 of the microfluidic device 101 as described below. The control logic can be configured by user input or a testing script or other suitable data structure, which is used to configure the controller or the computer processing system 145 to carry out control operations that are part of the workflow as described herein. For example, the user input or the testing script or other suitable data structure can specify parameters (such as pressures, flow rates, or temperatures) for such control operations of the workflow.

Figure 4:
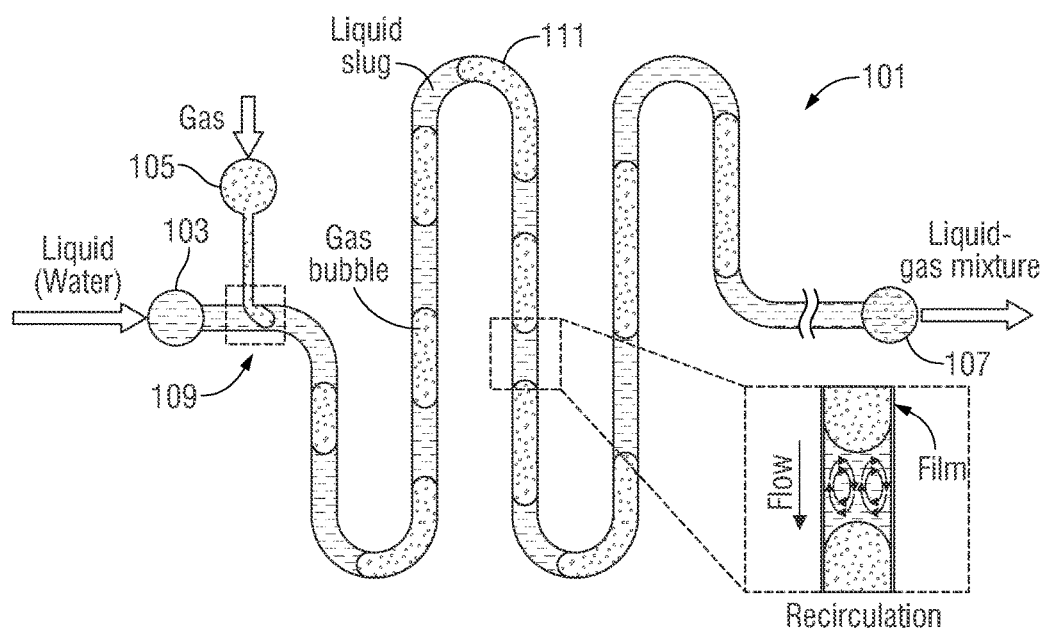
FIG. 4 is a schematic diagram showing the mixing process in the microchannel of the microfluidic device of FIG. 1 during operation of the test apparatus.
Figure 6A:
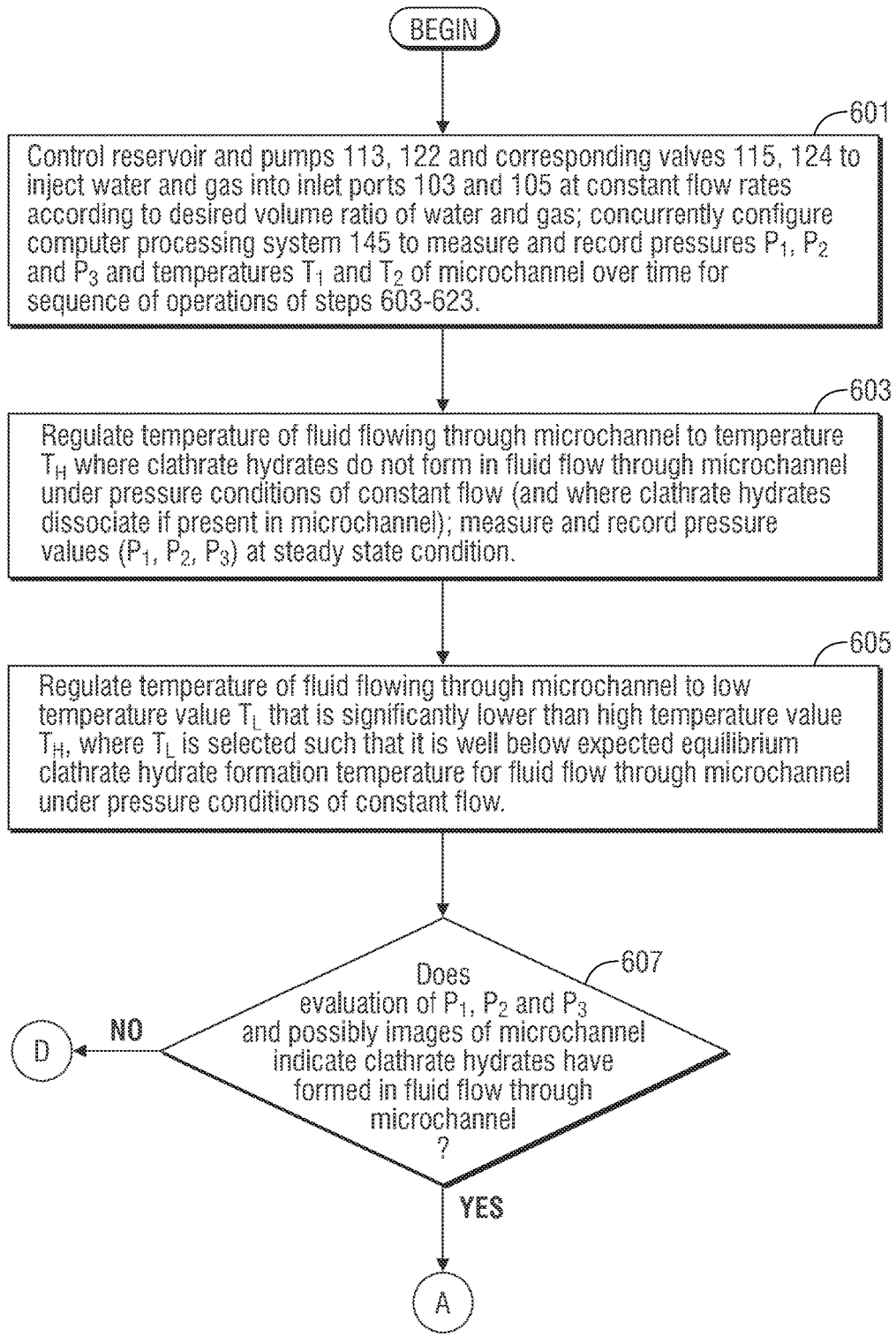
FIGS. 6A-6C are, collectively, a flow chart describing a sequence of test operations carried out by the test apparatus of FIG. 1 to characterize properties related to clathrate hydrate formation conditions of fluid that flows through the microchannel of the microfluidic device.
Figure 6B:
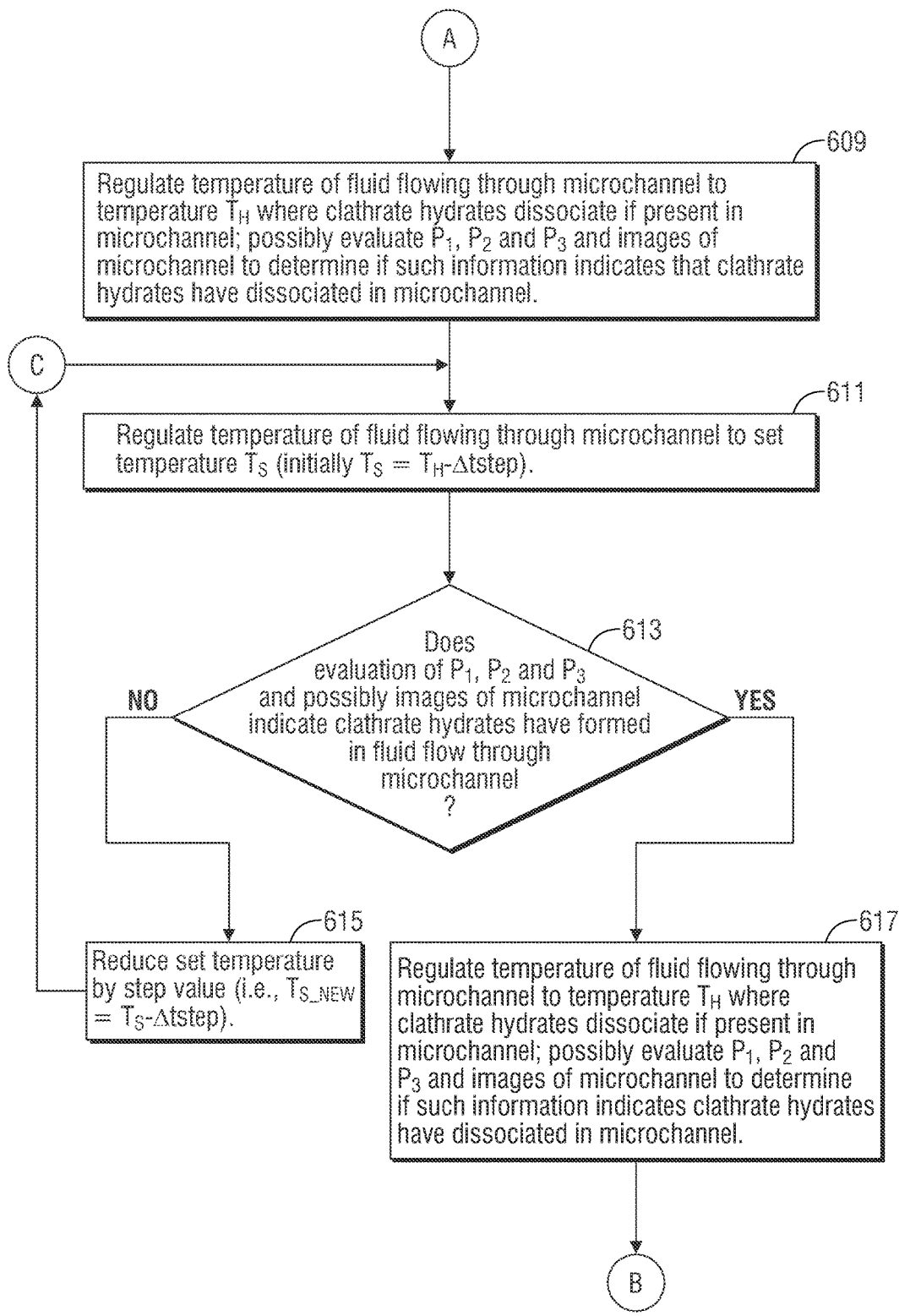
Figure 6C:
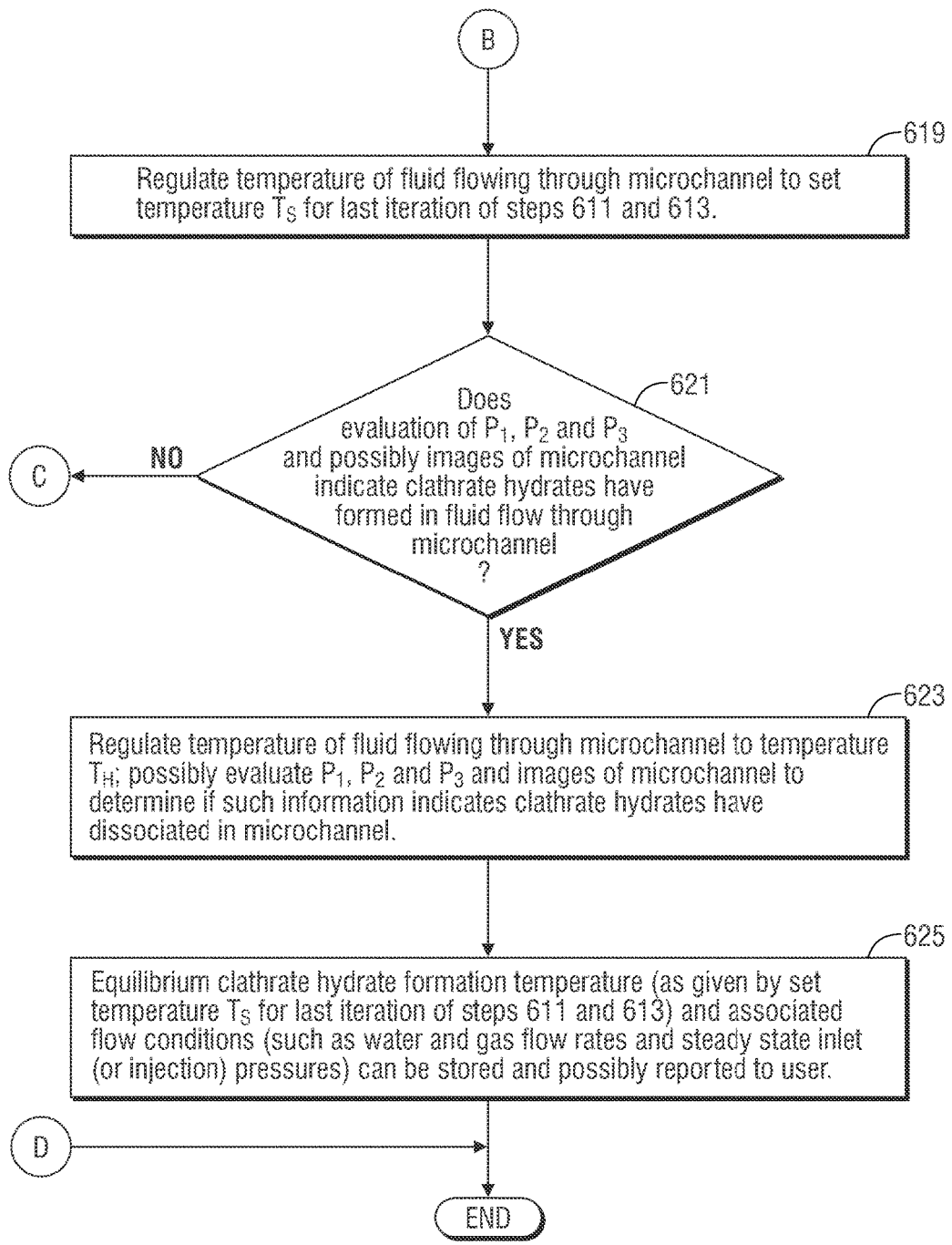

The workflow is illustrated in the flow chart of FIGS. 6A-6C. It is assumed that the reservoir and pump 113 is filled with a sufficient quantity of water and the reservoir and pump 122 is filled with a sufficient quantity of gas. The workflow begins in step 601 where the reservoir and pump 113 and the corresponding valve 115 are controlled to inject water into the first inlet port 103 of the microfluidic device 101 while the reservoir and pump 122 and the corresponding valve 124 are controlled to inject gas into the second inlet port 105 of the microfluidic device 101. The pumping rates for the pumps 113 and 122 are configured such that the water and gas are supplied to the inlet ports 103 and 105 at constant flow rates. The flow rates for the water and the gas dictate the relative volume ratios of water and gas for the test. The flow rates, and thus the resultant relative volume ratios of water and gas, can be varied over multiple iterations of the test as desired. The water and gas that are supplied to the inlet ports 103 and 105 flow to the mixing section 109 of the microfluidic device 101, which forms a segmented flow pattern of liquid water slugs and gas bubbles as shown in FIG. 4. The resultant liquid water slugs and gas bubbles mix as they flow through the microchannel 111 of the microfluidic device 101. Due to the large surface-to-volume ratio of the microchannel 111, the flow through the microchannel 111 exhibits excellent mass transfer between the co-flowing water and gas. The flow of mixed water and gas exits the microchannel 111 and flows out the outlet port 107 of the microfluidic device 101 to the collection chamber 129 via the outlet line 133.

Figure 7A:
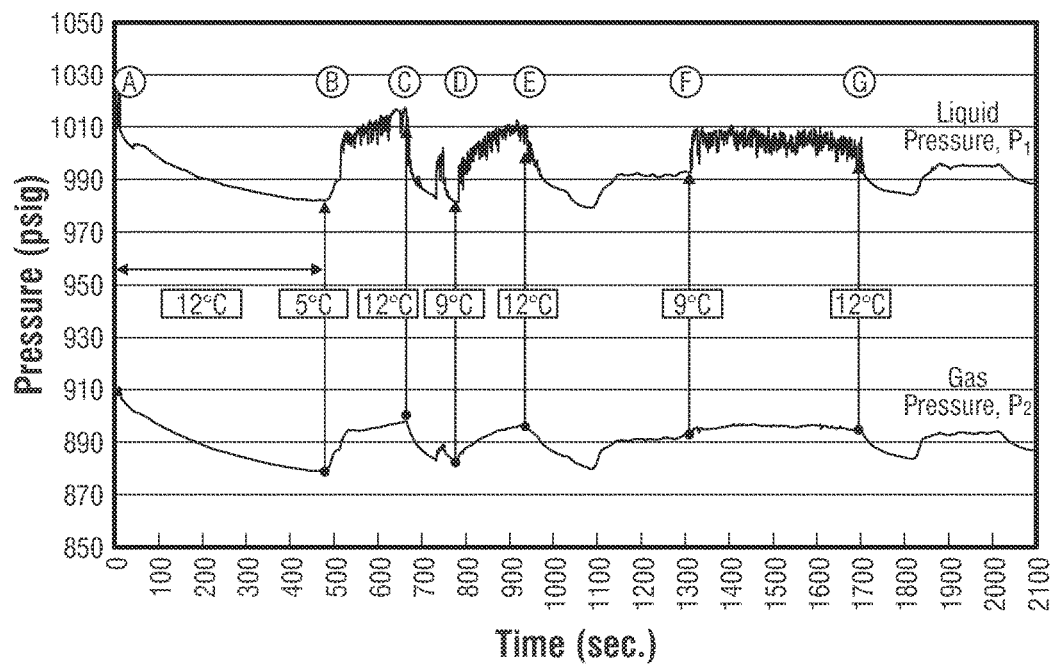
FIG. 7A is a plot of the inlet pressures $P_1$ and $P_2$ measured and recorded by the test apparatus of FIG. 1 over time as part of a sequence of test operations that follow the flow chart of FIGS. 6A-6C where a mixture of water and carbon dioxide gas flows through the microchannel of the microfluidic device.

Concurrent with the operations of step 601, the workflow carries out a sequence of operations in steps 603-623 that vary the temperature of the fluid flow through the microchannel 111 to determine properties related to the clathrate hydrate formation condition (such as the clathrate hydrate formation temperature) for the flow through the microchannel 111. In each of the steps 603-623, the temperature of the fluid flow through the microchannel 111 is controlled by regulating the temperature of the microchannel 111 via temperature control of the temperature-controlled cooling/heating surface 135. As mentioned earlier, temperature equilibration in the microchannel 111 can be achieved quickly due to the availability of large surface area as well as small fluid volume. During the operation of steps 603-623, pressures are measured by the pressure sensors 117, 125 and 131 and recorded by the computer processing system 145, and temperatures are measured by the temperature sensors 137 and 139 and recorded by the computer processing system 145. Such pressures and temperatures can also be displayed on graphs relative to time for user evaluation if desired. For example, FIG. 7A depicts a graph that shows the pressures ($P_1$ and $P_2$) measured by the pressure sensors 117 and 125, respectively, over time. Such pressures and temperatures can also be stored in the memory system of the computer processing system 145 for automated data analysis if desired.

In step 603, the temperature of the fluid flow through the microchannel 111 is regulated such that it is maintained at a high temperature value ($T_H$) where clathrate hydrates dissociate under the pressure conditions of the constant flow of the test if present in the microchannel 111. Thus, the high temperature value ($T_H$) is well above the equilibrium clathrate hydrate formation temperature for the constant flow conditions in the microchannel 111. After a time period where the pressure ($P_1$) measured by the pressure sensor 117 for the water and the pressure ($P_2$) measured by the pressure sensor 125 for the gas reach steady state values, the computer processing system 145 can record the steady state pressure values ($P_1$ and $P_2$) as well as the pressure ($P_3$) measured by the pressure sensor 131 at the steady state condition.

In step 605, the temperature of the fluid flow through the microchannel 111 is regulated to a low temperature value ($T_L$) that is significantly lower than the high temperature value ($T_H$) of step 603 and the operations continue to step 607. The low temperature value ($T_L$) is selected such that it is well below the expected equilibrium clathrate hydrate formation temperature for the fluid flow through the microchannel 111 under the pressure conditions of the constant flow of the test.

Figure 5:
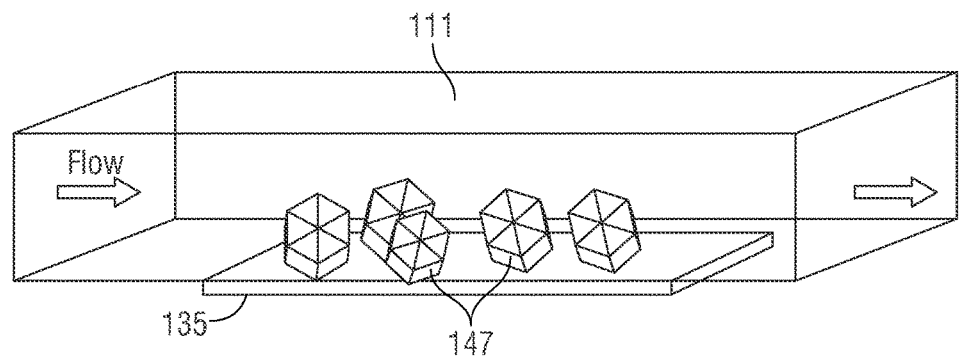
FIG. 5 is a schematic diagram showing clathrate hydrates deposited inside the microchannel of the microfluidic device of FIG. 1 during operation of the test apparatus.

In step 607, the pressures measured by the pressure sensors 117, 125 and 131 can be evaluated to determine whether such pressures indicate that clathrate hydrates have formed in the fluid flow through the microchannel 111. Specifically, an abrupt increase in pressure $P_1$ as compared to pressure $P_1$ under the steady state conditions as recorded in step 603 (and/or an abrupt increase in the relative pressure between pressure $P_1$ and outlet pressure $P_3$ as compared to the relative pressure between pressure $P_1$ and outlet pressure $P_3$ under the steady state conditions as recorded in step 603) concurrent with an abrupt increase in pressure $P_2$ as compared to pressure $P_2$ under the steady state conditions as recorded in step 603 (and/or an abrupt increase in the relative pressure between pressure $P_2$ and outlet pressure $P_3$ as compared to the relative pressure between pressure $P_2$ and outlet pressure $P_3$ under the steady state conditions as recorded in step 603) can provide an indication of clathrate hydrate formation in the microchannel 111. These abrupt increases in pressure at constant flow indicate higher flow resistance in the microchannel 111 caused by clathrate hydrate formation. It has also been found that pressure $P_1$ (and/or the relative pressure between pressure $P_1$ and outlet pressure $P_3$) can exhibit high frequency oscillations that are indicative of clathrate hydrate formation in the microchannel 111. Evaluation of pressure $P_1$ (and/or the relative pressure between pressure $P_1$ and outlet pressure $P_3$) for such high frequency oscillations can also be performed as part of the evaluation of step 607. FIG. 5 is a schematic representation of clathrate hydrates 147 formed in the microchannel 111. The light source 141 and the camera 143 can be used to capture one or more high resolution images of the microchannel 111 as part of the evaluation of step 607. Such image(s) can be displayed by the computer processing system 145 for evaluation by the operator/user to ascertain if clathrate hydrates are present in the image(s).

Note that the pressure drop across the microchannel 111 can be defined as the difference between the average inlet pressure (($P_1$+$P_2$)/2) and the outlet pressure $P_3$ of the microchannel 111. In a fully developed laminar flow through a circular channel, the pressure drop necessary for driving the liquid at a specified flow rate can be calculated by using the Hagen-Poiseuille equation as follows:

$$\Delta P = \frac{128\mu_L Q L}{\pi D_h^4} \tag{1}$$

where $\mu_L$ is the liquid viscosity,
Q is the average volumetric flow rate through the channel,
L is the total channel length and
$D_h$ (=4×cross-section/wetted perimeter) is the hydraulic diameter of the channel.

For a constant flow in a fixed-length channel, the pressure drop scales linearly with viscosity. However, the channel diameter has a significantly larger influence (fourth power of $D_h$) on the pressure drop. Therefore, a small variation in a channel cross-section or viscosity can be easily detected by monitoring the pressure drop. It should be noted that the surface-to-volume ratio varies as $D_h^{-1}$. Thus, in step 607, the pressure drop required for a constant flow in the microchannel 111 is expected to be considerably higher (based on Eq. 1) when clathrate hydrates form inside the microchannel 111 than in the case of simple fluid flow. The flow of the fluid carrying clathrate hydrates is analogous to the flow of particle suspensions, where the effective viscosity in the flow increases due to the presence of solid particles. Additionally, the deposition of hydrates on the internal surface of the channel also reduces the hydraulic diameter. Both of these effects contribute to an increase in the pressure drop in the microchannel 111 to maintain the volumetric flow.

In the event that the evaluation of step 607 determines that clathrate hydrates have formed in the fluid flow through the microchannel 111, the operations continue to step 609. Otherwise, the operations for the test end.

In step 609, the temperature of the fluid flow through the microchannel 111 is regulated such that it is maintained at the high temperature value ($T_H$) where clathrate hydrates dissociate under the pressure conditions of the constant flow of the test. This operation is intended to remove any clathrate hydrates that have deposited on the walls of the microchannel 111.

As part of step 609, the pressures measured by the pressure sensors 117, 125 and 131 can be evaluated to determine whether such pressures indicate that clathrate hydrates have dissociated under the pressure conditions of the constant flow through the microchannel 111. Specifically, an abrupt decrease in pressure $P_1$ together with a return to the steady state conditions as recorded in step 603 (and/or an abrupt decrease in the relative pressure between pressure $P_1$ and outlet pressure $P_3$ together with a return to the steady state conditions as recorded in step 603) concurrent with an abrupt decrease in pressure $P_2$ together with a return to the steady state conditions as recorded in step 603 (and/or an abrupt decrease in the relative pressure between pressure $P_2$ and outlet pressure $P_3$ together with a return to the steady state conditions as recorded in step 603) can provide an indication of clathrate hydrate dissociation in the microchannel 111. These abrupt decreases in pressure at constant flow as well as the return to steady state conditions indicate a decrease in flow resistance in the microchannel 111 caused by clathrate hydrate dissociation. Pressure $P_1$ (and/or the relative pressure between pressure $P_1$ and outlet pressure $P_3$) can also be evaluated as part of step 609 to ensure that the pressure signal has no high frequency oscillations that are indicative of clathrate hydrates in the microchannel 111. The light source 141 and camera 143 can also be used to capture one or more high resolution images of the microchannel 111 as part of step 609. Such image(s) can be displayed by the computer processing system 145 for evaluation by the operator/user to ascertain that clathrate hydrates are not present in the image(s). Such evaluation can be used to confirm that the clathrate hydrates have dissociated under the pressure conditions of the constant flow. In the event that this evaluation fails, step 609 can be repeated possibly at higher temperatures until it is confirmed that the clathrate hydrates have dissociated under the pressure conditions of the constant flow. The operations then continue to step 611.

In step 611, the temperature of the fluid flow through the microchannel 111 is regulated to a set temperature value ($T_S$) that is derived initially by subtracting a predetermined step value (such as 1° C. or 0.5° C.) from the high temperature value ($T_H$). The temperature change is typically performed following a ramp function over a period of time. The rate is selected by the user based on the test requirement and is programmed on the controller of the temperature-controlled cooling/heating surface 135. The temperature change can also be performed using small step functions.

In step 613, the pressures measured by the pressure sensors 117, 125 and 131 can be evaluated to determine whether such pressures indicate that clathrate hydrates have formed in the fluid flow through the microchannel 111. This evaluation can be carried out in an identical or similar manner to the evaluation of step 607 as described above. The light source 141 and camera 143 can also be used to capture one or more high resolution images of the microchannel 111. Such image(s) can be displayed by the computer processing system 145 for evaluation by the operator/user to ascertain if clathrate hydrates are present in the image(s).

In the event that the evaluation of step 613 determines that clathrate hydrates have not formed in the fluid flow through the microchannel 111, the operations continue to step 615 where the set temperature is reduced by the predetermined step value to a new set temperature and the operations return to repeat steps 611 and 613 to evaluate the fluid flow through the microchannel 111 at the new reduced set temperature. These iterative operations can be repeated multiple times if necessary until the evaluation of step 613 determines that clathrate hydrates have formed in the fluid flow through the microchannel 111. In this case, the set temperature value for the last iteration of steps 611 and 613 can be equated to the equilibrium clathrate hydrate formation temperature of the fluid flow through the microchannel 111 for the test and the operations continue to step 617.

In step 617, the temperature of the fluid flow through the microchannel 111 is regulated such that it is maintained at the high temperature value ($T_H$) where clathrate hydrates dissociate for the fluid flow through the microchannel 111. This operation is intended to remove any clathrate hydrates that have deposited on the walls of the microchannel 111. The pressures measured by the pressure sensors 117, 125 and 131 can be evaluated to determine whether such pressures indicate that clathrate hydrates have dissociated under the pressure conditions of the constant flow through the microchannel 111. This evaluation can be carried out in an identical or similar manner to the evaluation of step 609 as described above. The light source 141 and the camera 143 can also be used to capture one or more high resolution images of the microchannel 111. Such image(s) can be displayed by the computer processing system 145 for evaluation by the operator/user to ascertain that clathrate hydrates are not present in the image(s). The evaluation operations of step 617 can be used to confirm that the clathrate hydrates have dissociated under the pressure conditions of the constant flow of the test. In the event that this evaluation fails, step 617 can be repeated at higher temperatures until it is confirmed that the clathrate hydrates have dissociated under the pressure conditions of the constant flow. The operations then continue to step 619.

In step 619, the temperature of the fluid flow through the microchannel 111 is regulated to the temperature value of the last iteration of steps 611 and 613, which can be equated to the equilibrium clathrate hydrate formation temperature of the fluid flow through the microchannel 111 for the test.

In step 621, the pressures measured by the pressure sensors 117, 125 and 131 can be evaluated to determine whether such pressures indicate that clathrate hydrates have formed in the fluid flow through the microchannel 111. This evaluation can be carried out in an identical or similar manner to the evaluation of step 607 as described above. The light source 141 and the camera 143 can also be used to capture one or more high resolution images of the microchannel 111. Such image(s) can be displayed by the computer processing system 145 for evaluation by the operator/user to ascertain if clathrate hydrates are present in the image(s).

The operations of steps 619 and 621 are intended to check and verify that the equilibrium clathrate hydrate formation temperature of the fluid flow through the microchannel 111 as determined in the last iteration of steps 611 and 613 is correct. In the event that the determination of step 621 fails, the operations can return to repeat the operations of steps 611 to 621 and utilize smaller temperature step values to derive an accurate and repeatable determination of the equilibrium clathrate hydrate formation temperature of the fluid flow through the microchannel 111.

In the event that the operations of steps 619 and 621 verify that the equilibrium clathrate hydrate formation temperature of the fluid flow through the microchannel 111 as determined in the last iteration of steps 611 and 613 is correct, the operations continue to steps 623 and 625.

In step 623, the temperature of the fluid flow through the microchannel 111 is regulated such that it is maintained at the high temperature value ($T_H$) where clathrate hydrates dissociate for the fluid flow through the microchannel 111. This operation is intended to remove any clathrate hydrates that have deposited on the walls of the microchannel 111. The pressures measured by the pressure sensors 117, 125 and 131 can be evaluated to determine whether such pressures indicate that clathrate hydrates have dissociated under the pressure conditions of the constant flow through the microchannel 111. This evaluation can be carried out in an identical or similar manner to the evaluation of step 609 as described above. The light source 141 and the camera 143 can also be used to capture one or more high resolution images of the microchannel 111. Such image(s) can be displayed by the computer processing system 145 for evaluation by the operator/user to ascertain that clathrate hydrates are not present in the image(s). The evaluation operations of step 623 can be used to confirm that the clathrate hydrates have dissociated under the pressure conditions of the constant flow of the test. In the event that this evaluation fails, step 623 can be repeated at higher temperatures until it is confirmed that the clathrate hydrates have dissociated under the pressure conditions of the constant flow. The operations then continue to step 625.

In step 625, the properties of the clathrate hydrate formation condition as determined by the test (which can include the temperature equilibrium clathrate hydrate formation temperature and associated flow conditions, such as the water and gas flow rates and steady state inlet or injection pressures) can be stored by the computer processing system 145 and possibly reported to the user.

After step 625, the operations of the test end.

Note that the evaluation of steps 607, 613 and 621 can be carried out by visual interpretation of the pressure data and/or images of the microchannel 111 by the operator/user. For fully-automated and semi-automated implementations of the workflow, such evaluation can also possibly involve signal processing of the pressure data for $P_1$, $P_2$ and $P_3$ that is carried out by the computer processing system 145 to derive an indication of hydrate formation and/or can possibly involve image processing of the image(s) of the microchannel 111 that is carried out by the computer processing system 145 to detect the presence (or absence) of hydrates in the microchannel 111.

Note that the workflow can be repeated multiple times under different flow conditions to determine the equilibrium clathrate hydrate formation temperature of the fluid flow for the different flow conditions. The workflow can also be repeated multiple times with different volume ratios of the gas and water to determine the equilibrium clathrate hydrate formation temperature of the fluid flow for the different gas-water volume ratios.

FIG. 7A is a pressure plot of the pressures $P_1$ and $P_2$ measured by the pressure sensors 117 and 125 over time during test operations according to the workflow of FIGS. 6A-6C. In this case, the reservoir and pump 122 and associated valve 124 were configured to inject a stream of carbon dioxide gas at a constant flow rate of 200 μl/min into the second inlet port 105 of the microfluidic device 101, and the reservoir and pump 113 and valve 115 were configured to inject deionized water at a constant flow rate of 10 μl/min into the first inlet port 103 of the microfluidic device 101. The carbon dioxide gas and the water are mixed with a gas-to-water volume ratio of 20:1 at the mixer section (T-junction) 109 of the microfluidic device 101. The outlet pressure $P_3$ measured by the pressure sensor 131 was substantially constant at 200 psig (14.1 kg/square cm gauge). A temperature-controlled metal plate was placed in physical contact with (and thus thermally coupled to) the microfluidic device 101 to regulate the temperature of the flowing fluids inside the microchannel 111 of the microfluidic device 101. The points (A-G) on the plot of FIG. 7A are used to identify temporal change-points where the temperature of the temperature-controlled metal plate (and corresponding temperature of the microchannel 111) was changed in the test operations. At point A, the temperature of the temperature-controlled metal plate was set to 12° C. At point B, the temperature of the temperature-controlled metal plate was set to 5° C. At point C, the temperature of the temperature-controlled metal plate was set to 12° C. At point D, the temperature of the temperature-controlled metal plate was set to 9° C. At point E, the temperature of the temperature-controlled metal plate was set to 12° C. At point F, the temperature of the temperature-controlled metal plate was set to 9° C. At point G, the temperature of the temperature-controlled metal plate was set to 12° C.

The pressure measurements shown in FIG. 7A are obtained after the temperature of the microchannel 111 is reduced from 20° C. to 12° C. and sufficient time is provided for the pressure $P_1$ of the water inlet 103 and the pressure $P_2$ of the gas inlet 105 to reach steady state values. This operation corresponds to step 603 of the workflow as described above where the temperature value of 12° C. corresponds to the high temperature value ($T_H$) where clathrate hydrates dissociate under the pressure conditions of the constant flow of the test if present in the microchannel 111. Note, that the pressure curves between points A and B are smooth due to the absence of solids/particles in the flow that could block the microchannel 111.

At point B of FIG. 7A, the temperature of the microchannel 111 is reduced from 12° C. to 5° C. This operation corresponds to step 605 of the workflow as described above where the temperature value of 5° C. corresponds to the low temperature value ($T_L$) that is well below the expected equilibrium clathrate hydrate formation temperature for the fluid flow through the microchannel 111 under the pressure conditions of the constant flow of the test. Note that as soon as the temperature is reduced, the pressures $P_1$ and $P_2$ measured by sensors 117 and 125 experience an abrupt increase of approximately 20 psi (1.4 kg/square cm) simultaneously, while the outlet pressure $P_3$ remains constant. These abrupt increases of the measured inlet pressures $P_1$ and $P_2$ at constant flow indicate higher flow resistance in the microchannel 111. It is interesting to note that the pressure $P_1$ measured by the pressure sensor 117 oscillates (±10 psi, ±0.7 kg/square cm) at the temperature of point B. This oscillation is characteristic of flows in narrow channels where the flowing fluid contains solids/particles. In this case, the abrupt increase in the inlet pressures $P_1$ and $P_2$ and the oscillatory nature of the inlet pressure $P_1$ are considered to be an indication of clathrate hydrate formation.

Figure 7B:
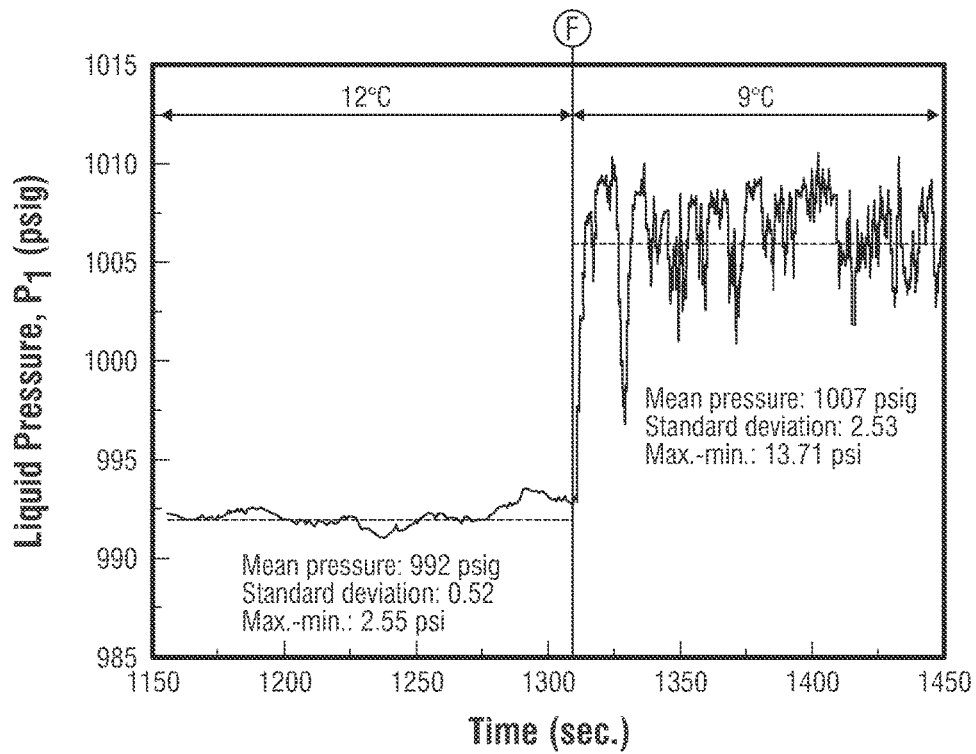
FIG. 7B is a detailed view of a part of the plot of FIG. 7A for a small period of time.

FIG. 7B depicts a section of the plot of FIG. 7A over a small time period (1150-1450 seconds) around the temperature point F (transition from 12° C. to 9° C.) This section shows in detail the abrupt increase in the inlet pressure $P_1$ measured by the pressure sensor 117 (e.g., the average (or mean) pressure increases from 992 psig (69.7 kg/square cm gauge) to 1007 psig (70.8 kg/square cm gauge) for a pressure increase of 15 psi (1.1 kg/square cm)) as well as the oscillatory nature of the inlet pressure $P_1$ for the case where clathrate hydrates have formed in the microchannel 111. Specifically, the inlet pressure $P_1$ for the water over the small time interval (1150-1450 seconds) where the temperature point was maintained at 12° C. had an average pressure of 992 psig (69.7 kg/square cm gauge) with standard deviation of 0.52. The absolute difference between the maximum and minimum pressure value for the inlet pressure $P_1$ during this time was 2.55 psi (0.2 kg/square cm). When the temperature was reduced to 9° C., the average inlet pressure $P_1$ increased to 1007 psig (70.8 kg/square cm gauge) (an average pressure increase ΔP of 15 psi (1.1 kg/square cm)) and the standard deviation was 2.53. The pressure fluctuation in the 9° C. temperature zone was significantly greater than that of the pressure profile in the 12° C. temperature zone. The absolute difference between the maximum and minimum pressure value during this time was 13.71 psi (1.0 kg/square cm). The mean pressure increment between the two temperature zones depends on several factors such as flow rate, liquid viscosity, and amount of hydrate particles in the liquid stream. However, the data shows that the change in the pressure profile (i.e., oscillation) is repeatable and can be used for an accurate discriminator of clathrate hydrate formation. In an automated system, the controller or computing system 145 can be programmed to process the pressure data and measure the change in pressure profile (increment in mean pressure and emergence of oscillation) based on signal processing algorithms. This provides an automated platform for the detection of clathrate hydrate formation conditions for the flow through the microchannel 111 of the microfluidic device 103 during the test operations.

Figure 8A:
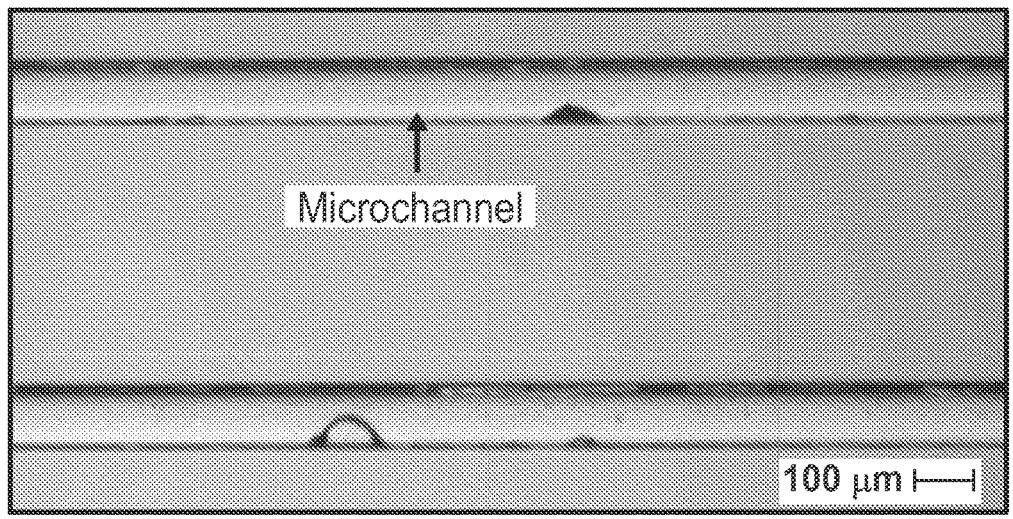
FIGS. 8A and 8B are images of the microchannel of the microfluidic device as captured by the camera of FIG. 1 during different parts of the exemplary test operations of FIG. 7A.
Figure 8B:
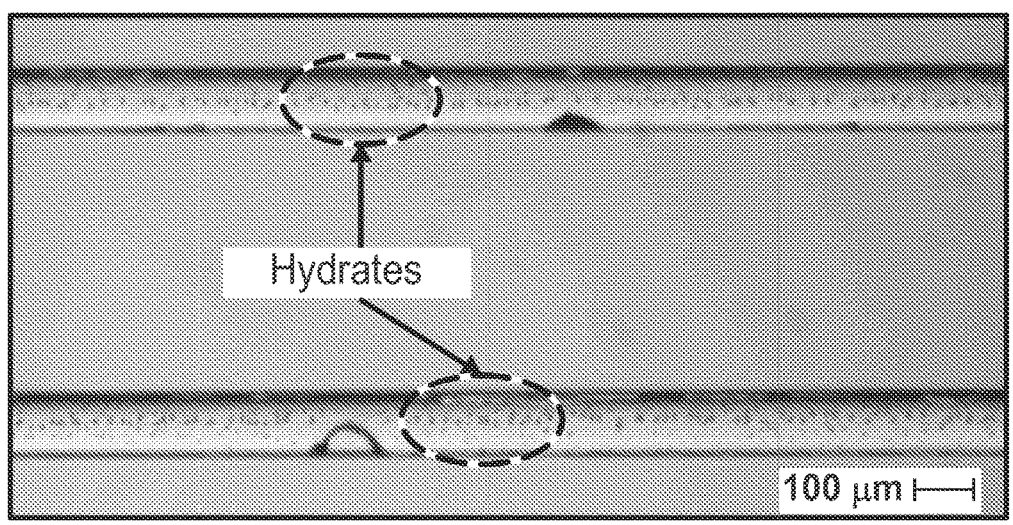

The indication of clathrate hydrate formation at the temperature point B of 5° C. was visually confirmed by configuring the light source 141 and camera 143 to capture close-up images of the microchannel 111 at temperatures of 12° C. (step 603) and at 5° C. (step 605) as shown in FIGS. 8A and 8B. FIG. 8A shows that the microchannel surface appears clean at 12° C. (step 603), whereas FIG. 8B shows that the microchannel surface appears spotted with dark clathrate hydrates at 5° C. (step 605).

At point C of FIG. 7A, the temperature of the microchannel 111 is increased from 5° C. to 12° C., which is intended to dissociate the clathrate hydrates in the microchannel 111. This operation corresponds to step 609 of the workflow as described above. The pressures $P_1$ and $P_2$ measured by the pressure sensors 117 and 125 both decrease with the temperature increase at point C and return to their respective steady state values (step 603) as shown. The oscillation in the pressure signal $P_1$ also disappears with the temperature increase at point C. The pressure decrease and the disappearance of the oscillations are correlated to the dissociation of the hydrates at 12° C. These indications of clathrate hydrate dissociation can be visually confirmed by configuring the light source 141 and camera 143 to capture close-up images of the microchannel 111 at 12° C., which should show that the clathrate hydrates have disappeared and the microchannel section is visibly clean similar to the image shown in FIG. 8A.

At point D of FIG. 7A, the temperature of the microfluidic device is decreased from 12° C. to 9° C. at a rate of approximately 10° C. per minute, nearly a step function. This operation corresponds to steps 611-615 of the workflow as described above. Note that when the temperature is reduced to 9° C., the inlet pressures $P_1$ and $P_2$ measured by both sensors 117 and 125 experience an abrupt increase simultaneously, while the outlet pressure $P_3$ remains constant. The inlet pressure $P_1$ measured by the pressure sensor 117 also exhibits oscillation at a temperature of 9° C. In this case, the abrupt increase in the inlet pressures $P_1$ and $P_2$ and the oscillatory nature of the inlet pressure P1 are considered to be an indication of clathrate hydrate formation. Note that the temperature of the microchannel 111 is maintained at 9° C. between points D and E of the test. This indication of clathrate hydrate formation can be visually confirmed by configuring the light source 141 and camera 143 to capture close-up images of the microchannel 111 at 9° C., where it is expected that the microchannel surface will appear spotted with dark clathrate hydrates similar to FIG. 8B.

At point E of FIG. 7A, the temperature of the microchannel 111 is increased from 9° C. to 12° C., which is intended to dissociate the clathrate hydrates in the microchannel 111. This operation corresponds to step 617 of the workflow described above. The pressures $P_1$ and $P_2$ measured by the pressure sensors 117 and 125 both decrease with the temperature increase at point E and return to their respective steady state values (step 603) as shown. The oscillation in the pressure signal $P_1$ also disappears with the temperature increase at point E. The pressure decrease and the disappearance of the oscillations are correlated to the dissociation of the hydrates at 12° C. These indications of clathrate hydrate dissociation can be visually confirmed by configuring the light source 141 and camera 143 to capture close-up images of the microchannel 111 at 12° C., which should show that the clathrate hydrates have disappeared and the microchannel section is visibly clean similar to that shown in FIG. 8A.

To confirm the formation of clathrate hydrates at 9° C., the temperature cycle from 12° C. to 9° C. and back to 12° C. is repeated at points F and G of FIG. 7. These operations correspond to steps 619 to 623 of the workflow described above.

In the test of FIG. 7A, the formation of clathrate hydrates is detected at 9° C. for the specific flow conditions and fluid sample types. The duration of the entire test is 35 minutes.

Figure 9:
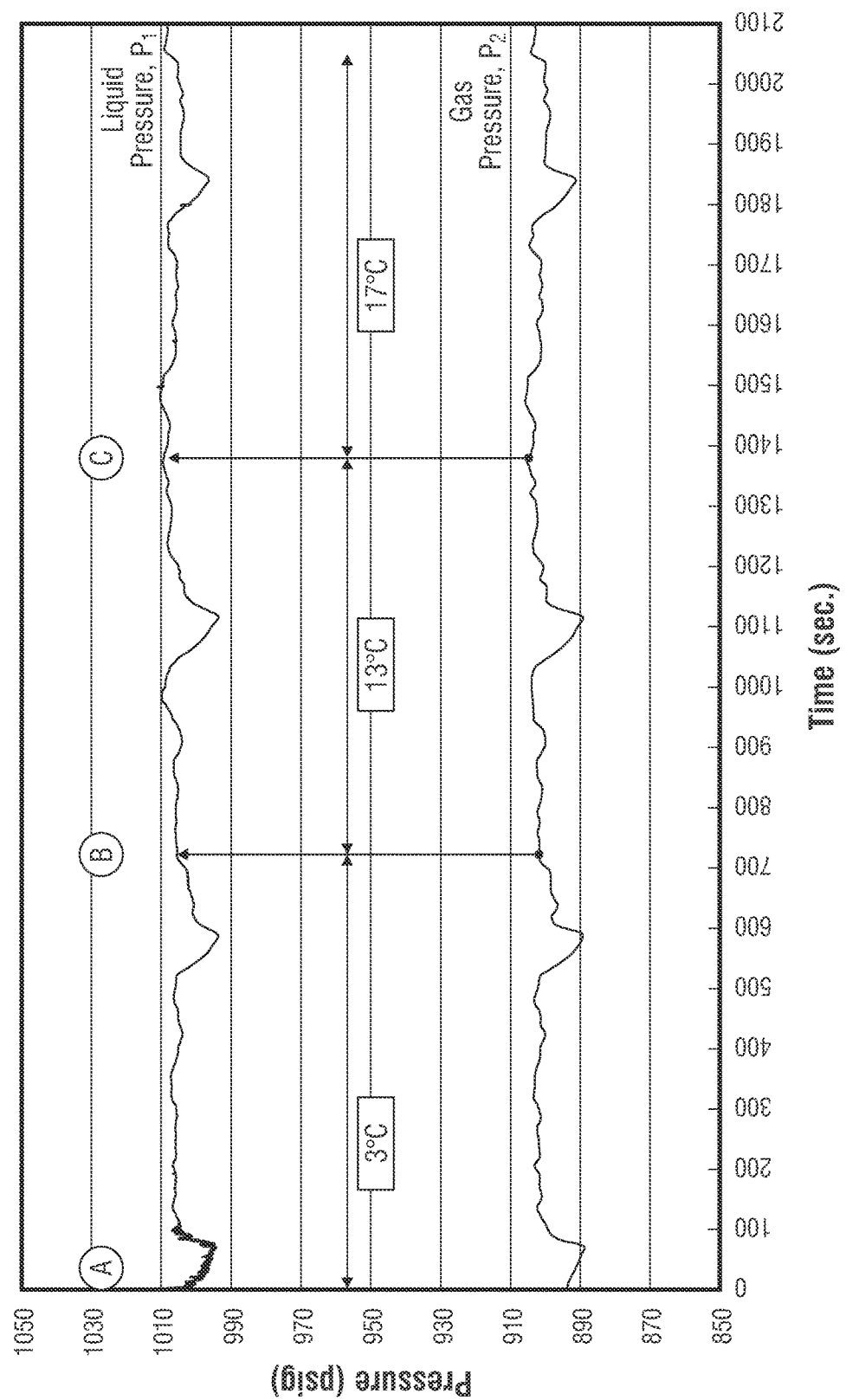
FIG. 9 is a plot of the inlet pressures $P_1$ and $P_2$ measured and recorded by the test apparatus of FIG. 1 over time as part of a sequence of test operations that follow the flow chart of FIGS. 6A-6C where a mixture of water/methanol and carbon dioxide gas flows through the microchannel of the microfluidic device.

The test was repeated with methanol added to the water injected into the first inlet port 103 of the microfluidic device 111 during the test. Methanol is a well-known hydrate inhibitor. Specifically, the reservoir and pump 113 and valve 115 were configured to inject a mixture of deionized water and methanol (20 percent methanol by weight) at a constant flow rate of 10 µl/min into the first inlet port 103 of the microfluidic device 101, and the reservoir and pump 122 and associated valve 124 were configured to inject a stream of carbon dioxide gas at a constant flow rate of 200 µl/min into the second inlet port 105 of the microfluidic device 101. The same temperature control operations were followed as described above with respect to the test of FIG. 7A. The inlet pressures ($P_1$ and $P_2$) and temperatures during this test are shown in FIG. 9. The outlet pressure $P_3$ was substantially constant at 250 psig (17.6 kg/square cm gauge) during the test. In this case, the low temperature $T_L$ was set to 3° C. (point A of FIG. 9 corresponding to step 605) to induce clathrate hydrate formation (where the low temperature $T_L$ of 5° C. was used in the previous test of FIG. 7A). However, pressure values for the inlet pressures $P_1$ and $P_2$ remained relatively constant. The pressure increase and oscillation observed in the previous test with clathrate hydrates were not observed during this period. The temperature was then increased to 13° C. at point B and then further to 17° C. at point C to detect any change due to temperature rise. The variation in the pressures $P_1$, $P_2$ was negligible at 13° C. (point B to point C) and also at 17° C. (point C onwards). However, the pressures $P_1$, $P_2$ at the different temperatures (points A-B-C) show a periodic oscillation which is most likely caused by air bubbles trapped in the flow lines. Therefore, the test apparatus (and the workflow of FIGS. 6A-6C) successfully demonstrated the effectiveness of methanol in preventing clathrate hydrate formation.

Figure 10:
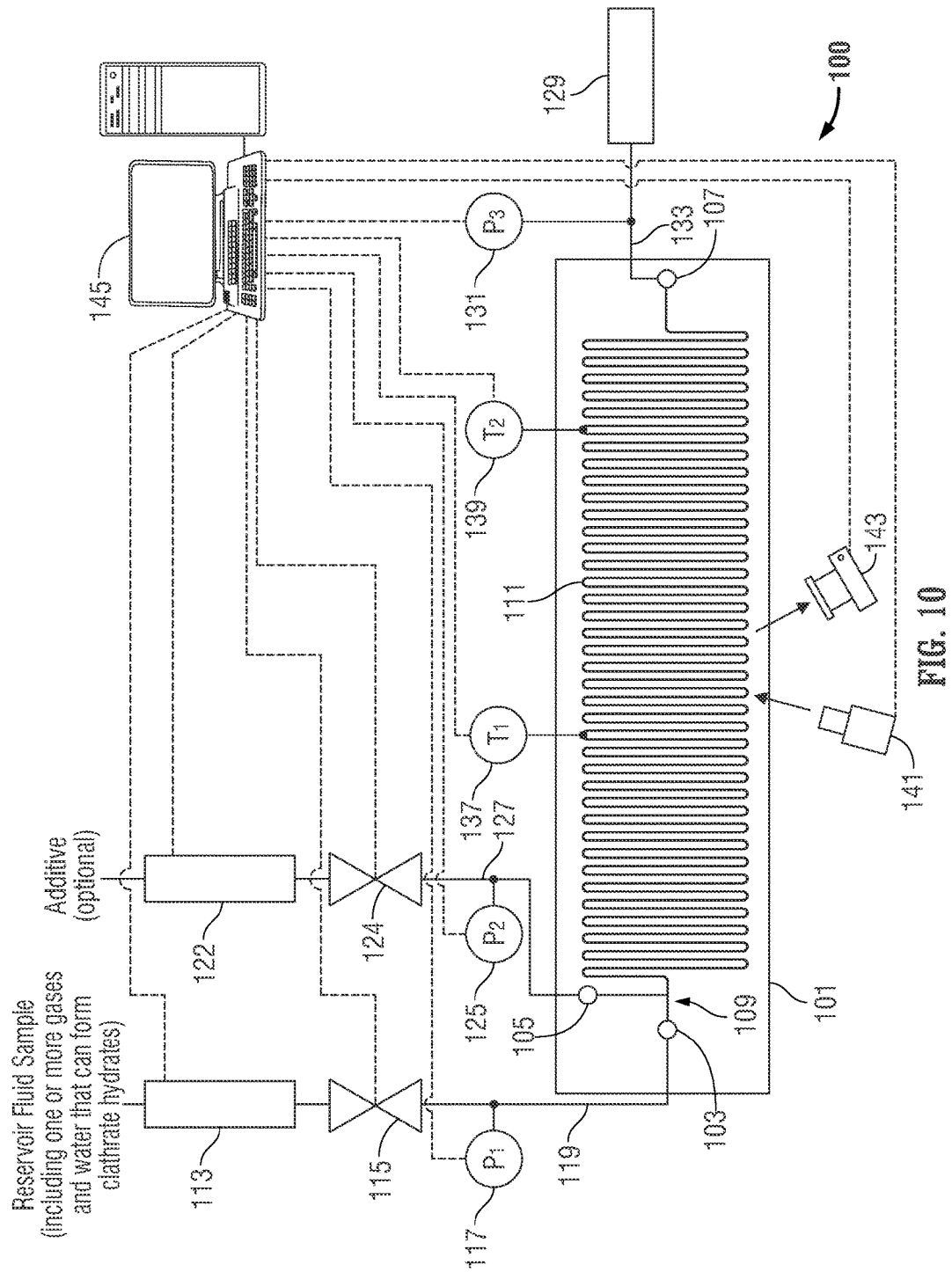
FIG. 10 is a schematic diagram of a test apparatus according to an embodiment of the present disclosure, where a fluid that includes a reservoir fluid component and possibly an additive flows through the microchannel of the microfluidic device during operation of the test apparatus. In this case, the test apparatus can be used to characterize properties related to clathrate hydrate formation conditions of the fluid that flows through the microchannel of the microfluidic device.

The test apparatus (and the workflow of FIGS. 6A-6C) as described herein can readily be adapted to characterize properties of clathrate hydrate formation condition for a reservoir fluid sample as depicted in FIG. 10. In this case, the reservoir and pump 113 is filled with a sufficient quantity of a reservoir fluid. The reservoir fluid can be extracted from the reservoir under reservoir temperature and pressure conditions via downhole fluid sampling. Alternatively, the reservoir fluid can be extracted from tubing or a transportation pipeline. The reservoir fluid can include one or more gases and water that can form clathrate hydrates under the appropriate temperature and pressure conditions. The reservoir and pump 122 can optionally be filled with a sufficient quantity of an additive (such as methanol) that inhibits formation of clathrate hydrates when mixed with the reservoir fluid. In this case, the workflow begins in step 601 where the reservoir and pump 113 and the corresponding valve 115 are controlled to inject the reservoir fluid into the first inlet port 103 of the microfluidic device 101 while the reservoir and pump 122 and the corresponding valve 124 are optionally controlled to inject the additive into the second inlet port 105 of the microfluidic device 101 (if desired). The pumping rates for the pumps 113 and 122 are configured such that the reservoir fluid and the additive (when used) are supplied to the inlet ports 103 and 105 at constant flow rates. The flow rates for the reservoir fluid and the additive dictate the relative volume ratios of reservoir fluid and the additive for the test. The reservoir fluid sample and the additive (if any) that are supplied to the inlet ports 103 and 105 flow to the mixing section 109 of the microfluidic device 101 and then through the microchannel 111 of the microfluidic device 101 and out the outlet port 107 of the microfluidic device 101 to the collection chamber 129 via the outlet line 133. Concurrent with the operations of step 601, the workflow carries out a sequence of operations in steps 603-623 that vary the temperature of the fluid flow through the microchannel 111 to determine clathrate hydrate formation temperature for the flow through the microchannel 111. The temperature points for such operations (such as the high temperature $T_H$ and the low temperature $T_L$) can be adjusted as needed for the particular reservoir fluid, the particular additive, the relative concentration of the additive and reservoir fluid for the flow through the microchannel 111 of the microfluidic device 101 and the pressure conditions of such flow. In this case, an abrupt increase in the inlet pressures $P_1$ and $P_2$ and the oscillatory nature of the inlet pressure $P_1$ are considered to be an indication of clathrate hydrate formation in the reservoir fluid/additive mixture flowing through the microchannel 111 of the microfluidic device 101 similar to the operations described above for the water/gas mixture. Similarly, a decrease in the inlet pressures $P_1$ and $P_2$ together with a lack of oscillations in the inlet pressure $P_1$ are considered to be an indication of clathrate hydrate dissociation in the reservoir fluid/additive mixture fluid flowing through the microchannel 111 of the microfluidic device 101 similar to the operations described above for the water/gas mixture. For the case where the additive is not used, the valve 124 can be closed and the pressure $P_2$ measured by the pressure sensor 125 can be ignored in the analysis.

The flow rates and thus the resultant relative volume ratios of reservoir fluid and additive can be varied over multiple iterations of the test to study clathrate hydrate formation temperature for different flow pressures and/or additive concentrations as desired. Similarly, the multiple iterations of the tests can be repeated with different additives to study the effects of different hydrate inhibitors on the particular reservoir fluid sample for different flow pressures and/or additive concentrations as desired. Such operations can be used to optimize a strategy for reservoir fluid production and/or transportation that minimizes the formation of clathrate hydrates during these processes.

The test apparatus and the workflow as described herein provide the following advantages:

Rapid hydrate detection

Suitability for a wellsite environment

Excellent repeatability

High quality data, comparable to conventional pressure-volume-temperature (PVT) lab measurements Small sample volume requirement Operator independent Suitable for inhibitor screening Potential for automation.

There have been described and illustrated herein several embodiments of a test apparatus and method that employs a microfluidic device to characterize properties of clathrate hydrate formation of a fluid. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A test apparatus for characterizing properties of a fluid, comprising:

a microfluidic device having a first inlet port, an outlet port, and a microchannel as part of a fluid path between the first inlet port and the outlet port;

a temperature-controlled surface that is thermally-coupled to the microfluidic device and configured to control temperature of the microchannel of the microfluidic device;

a first pump fluidly coupled to the first inlet port of the microfluidic device, wherein the first pump is operated to generate a flow of the fluid through the microchannel of the microfluidic device;

a first pressure sensor configured to measure fluid pressure at the first inlet port of the microfluidic device; and means for recording fluid pressure measured by the first pressure sensor over time as the temperature-controlled surface is operated to vary temperature of the microchannel of the microfluidic device to characterize properties of the fluid.

2. A test apparatus according to claim 1, further comprising at least one temperature sensor for measuring temperature characteristic of the microchannel of the microfluidic device.

3. A test apparatus according to claim 1, wherein the properties of the fluid relate to the clathrate hydrate formation condition of the fluid at the pressure of the flow through the microchannel of the microfluidic device.

4. A test apparatus according to claim 3, wherein the properties of the fluid include the clathrate hydrate formation temperature of the fluid at the pressure of the flow through the microchannel of the microfluidic device.

5. A test apparatus according to claim 3, further comprising a light source and camera configured to capture images of the microchannel of the microfluidic device.

6. A test apparatus according to claim 5, wherein the test apparatus is configured to evaluate or analyze the images captured by the camera to determine whether such images include information that indicates the presence of clathrate hydrate formation in the fluid that flows through the microchannel of the microfluidic device.

7. A test apparatus according to claim 3, further comprising means for evaluating or analyzing the fluid pressure measured by the first pressure sensor over time as the temperature-controlled surface is operated to vary temperature of the microchannel of the microfluidic device to determine whether the fluid pressure measured by the first pressure sensor over time includes characteristics that indicate the presence of clathrate hydrate formation in the fluid that flows through the microchannel of the microfluidic device.

8. A test apparatus according to claim 7, wherein the characteristics that indicate the presence of clathrate hydrate formation in the fluid that flows through the microchannel of the microfluidic device are selected from the group consisting of i) an increase in the fluid pressure measured by the first pressure sensor and ii) oscillations in the fluid pressure measured by the first pressure sensor.

9. A test apparatus according to claim 1, wherein the first pump is configured to supply a reservoir fluid to the first inlet port of the microfluidic device such that the fluid flowing through the microchannel of the microfluidic device includes the reservoir fluid.

10. A test apparatus according to claim 1, wherein the first pump is configured such that the fluid flows through the microchannel of the microfluidic device at a constant flow rate.

11. A test apparatus according to claim 1, wherein the microfluidic device further includes a second inlet port and a mixing section that is fluidly coupled to both the first inlet port and the second inlet port, wherein the microchannel is part of a fluid path between the mixing section and the outlet port of the microfluidic device.

12. A test apparatus according to claim 11, further comprising:
a second pump fluidly coupled to the second inlet port of the microfluidic device, wherein the first pump and the second pump are configured to generate the flow of the fluid through the microchannel of the microfluidic device;
a second pressure sensor for measuring fluid pressure at the second inlet port of the microfluidic device; and
means for recording fluid pressure measured by the second pressure sensor over time as the temperature-controlled surface is operated to vary temperature of the microchannel of the microfluidic device to characterize properties of the fluid.

13. A test apparatus according to claim 12, further comprising means for evaluating or analyzing the fluid pressures measured by the first and second pressure sensors over time as the temperature-controlled surface is operated to vary temperature of the microchannel of the microfluidic device to determine whether the fluid pressures measured by the first and second pressure sensors over time include characteristics that indicate the presence of clathrate hydrates in the fluid that flows through the microchannel of the microfluidic device.

14. A test apparatus according to claim 12, wherein the first pump is configured to supply a reservoir fluid to the first inlet port of the microfluidic device and the second pump is configured to supply an additive to the second inlet port of the microfluidic device such that the fluid that flows through the microchannel of the microfluidic device includes a mixture of the reservoir fluid and the additive.

15. A test apparatus according to claim 12, wherein the first pump and the second pump are configured such that the fluid flows through the microchannel of the microfluidic device at a constant flow rate.

16. A test method for characterizing properties of a fluid, comprising:
providing a microfluidic device having a first inlet port, an outlet port, and a microchannel as part of a fluid path between the first inlet port and the outlet port;
while generating a flow of the fluid through the microchannel of the microfluidic device, measuring and recording fluid pressure at the first inlet port of the microfluidic device in conjunction with varying temperature of the microchannel of the microfluidic device to characterize properties of the fluid that flows through the microchannel of the microfluidic device.

17. A test method according to claim 16, wherein the properties of the fluid relate to the clathrate hydrate formation condition of the fluid at the pressure of the flow through the microchannel of the microfluidic device.

18. A test method according to claim 17, wherein the properties of the fluid include the clathrate hydrate formation temperature of the fluid at the pressure of the flow through the microchannel of the microfluidic device.

19. A test method according to claim 17, further comprising while generating a flow of the fluid through the microchannel of the microfluidic device, capturing images of the microchannel of the microfluidic device.

20. A test method according to claim 19, further comprising evaluating or analyzing the captured images to determine whether such images include information that indicates the presence of clathrate hydrate formation in the fluid that flows through the microchannel of the microfluidic device.

21. A test method according to claim 17, further comprising evaluating or analyzing the fluid pressure at the first inlet port over time as the temperature of the microchannel of the microfluidic device is varied to determine whether the fluid pressure measured by the first pressure sensor over time includes characteristics that indicate the presence of clathrate hydrate formation in the fluid that flows through the microchannel of the microfluidic device.

22. A test method according to claim 21, wherein the characteristics that indicate the presence of clathrate hydrate formation in the fluid that flows through the microchannel of the microfluidic device are selected from the group consisting of i) an increase in the fluid pressure at the first inlet port and ii) oscillations in the fluid pressure at the first inlet port.

23. A test method according to claim 16, further comprising configuring a first pump to supply a reservoir fluid to the first inlet port of the microfluidic device such that the fluid flowing through the microchannel of the microfluidic device includes the reservoir fluid.

24. A test method according to claim 16, further comprising configuring a first pump such that the fluid flows through the microchannel of the microfluidic device at a constant flow rate.

25. A test method according to claim 16, wherein:
the microfluidic device further includes a second inlet port and a mixing section that is fluidly coupled to both the first inlet port and the second inlet port; and
wherein the microchannel is part of a fluid path between the mixing section and the outlet port of the microfluidic device.

26. A test method according to claim 25, further comprising while generating the flow of the fluid through the microchannel of the microfluidic device, measuring and recording fluid pressure at the second inlet port of the microfluidic device in conjunction with varying temperature of the microchannel of the microfluidic device to characterize properties of the fluid that flows through the microchannel of the microfluidic device.

27. A test method according to claim 25, further comprising evaluating or analyzing the fluid pressures at the first and second inlet ports over time as the temperature of the microchannel of the microfluidic device is varied to determine whether the fluid pressures at the first and second inlet ports over time include characteristics that indicate the presence of clathrate hydrate formation in the fluid that flows through the microchannel of the microfluidic device.

28. A test method according to claim 25, further comprising configuring a first pump to supply a reservoir fluid to the first inlet port of the microfluidic device and configuring a second pump to supply an additive to the second inlet port of the microfluidic device such that the fluid that flows through the microchannel of the microfluidic device includes a mixture of the reservoir fluid and the additive.

29. A test method according to claim 25, wherein configuring a first pump to supply a first fluid to the first inlet port of the microfluidic device and configuring a second pump to supply a second fluid to the second inlet port of the microfluidic device such that the fluid that flows through the microchannel of the microfluidic device is a mixture including first and second fluids that flows at a constant flow rate.

30. A test method for characterizing properties that relate to the clathrate hydrate formation condition of a fluid that includes a reservoir fluid component, comprising:
 providing a microfluidic device having a first inlet port, an outlet port, and a microchannel as part of a fluid path between the first inlet port and the outlet port; and
 while generating a flow of the fluid through the microchannel of the microfluidic device, measuring and recording fluid pressure at the first inlet port of the microfluidic device in conjunction with varying temperature of the microchannel of the microfluidic device to characterize properties that relate to the clathrate hydrate formation condition of the fluid at the pressure of the flow through the microchannel of the microfluidic device.

31. A test method according to claim 30, further comprising configuring a first pump to supply a reservoir fluid to the first inlet port of the microfluidic device such that the fluid flowing through the microchannel of the microfluidic device includes the reservoir fluid.

32. A test method according to claim 30, further comprising while the temperature of the microchannel of the microfluidic device is controlled to a temperature where clathrate hydrates dissociate at the pressure of the flow through the microchannel of the microfluidic device, measuring and recording a steady state fluid pressure at the first inlet port of the microfluidic device.

33. A test method according to claim 30, further comprising while iteratively decreasing the temperature of the microchannel of the microfluidic device by a predetermined step value, evaluating or analyzing the fluid pressure at the first inlet port over time to determine whether the fluid pressures at the first inlet port over time include characteristics that indicate the presence of clathrate hydrate formation in the fluid that flows through the microchannel of the microfluidic device.

34. A test method according to claim 33, further comprising:
 subsequent to determining the presence of clathrate hydrate formation in the fluid that flows through the microchannel of the microfluidic device, increasing the temperature of the microchannel of the microfluidic device to a temperature where clathrate hydrates dissociate at the pressure of the flow through the microchannel of the microfluidic device; and
 with the temperature of the microchannel of the microfluidic device controlled at the temperature where clathrate hydrates dissociate at the pressure of the flow through the microchannel of the microfluidic device, evaluating or analyzing the fluid pressure at the first inlet port over time to determine whether the fluid pressures at the first inlet port over time include characteristics that indicate the absence of clathrate hydrate formation in the fluid that flows through the microchannel of the microfluidic device.

35. A test method according to claim 30, wherein:
 the microfluidic device further includes a second inlet port and a mixing section that is fluidly coupled to both the first inlet port and the second inlet port, wherein the microchannel is part of a fluid path between the mixing section and the outlet port of the microfluidic device; and
 wherein the method further comprises configuring a first pump to supply a reservoir fluid to the first inlet port of the microfluidic device and configuring a second pump to supply an additive to the second inlet port of the microfluidic device such that the fluid that flows through the microchannel of the microfluidic device includes a mixture of the reservoir fluid and the additive.

* * * * *